United States Patent
Ortiz et al.

(10) Patent No.: US 12,226,087 B2
(45) Date of Patent: Feb. 18, 2025

(54) RETRACTOR

(71) Applicant: Spinal Elements, Inc., Carlsbad, CA (US)

(72) Inventors: David Ortiz, Oceanside, CA (US); Kyle Elsabee, San Diego, CA (US); Jason Blain, Encinitas, CA (US); Tyson Vogel, San Diego, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 1025 days.

(21) Appl. No.: 17/188,207

(22) Filed: Mar. 1, 2021

(65) Prior Publication Data
US 2021/0244398 A1 Aug. 12, 2021

Related U.S. Application Data

(63) Continuation of application No. 16/082,797, filed as application No. PCT/US2017/019699 on Feb. 27, 2017, now Pat. No. 10,973,505.
(Continued)

(51) Int. Cl.
*A61B 1/32* (2006.01)
*A61B 17/02* (2006.01)

(52) U.S. Cl.
CPC ............ *A61B 17/0206* (2013.01); *A61B 1/32* (2013.01); *A61B 2017/0256* (2013.01)

(58) Field of Classification Search
CPC ........ A61B 17/0206; A61B 2017/0262; A61B 17/025; A61B 2017/0256; A61B 1/32;
(Continued)

(56) References Cited

U.S. PATENT DOCUMENTS

| | | |
|---|---|---|
| 350,721 A | 10/1886 | Cooper |
| 569,839 A | 10/1896 | Roeloffs |
| (Continued) | | |

FOREIGN PATENT DOCUMENTS

| | | |
|---|---|---|
| EP | 2 705 799 | 3/2014 |
| JP | 2010-508978 | 3/2010 |
| (Continued) | | |

OTHER PUBLICATIONS

Official Communication in European Application No. 20180562.9, dated Sep. 18, 2020.
(Continued)

*Primary Examiner* — Lynnsy M Summitt
(74) *Attorney, Agent, or Firm* — Knobbe, Martens, Olson & Bear, LLP

(57) ABSTRACT

A retractor for use in surgical operations comprises a pair of blade assemblies. In operation, the blade assemblies are initially in a closed position to assume a low profile, inserted into a relatively small incision, and stretched apart from each other, thereby stretching the skin about the incision to form an aperture longer than the incision. The retractor is adapted to rotate a first blade about a first axis and a second blade about a second axis. The retractor is adapted to move the pair of blade assemblies apart along a third axis. The retractor is adapted to pivot the first blade about a fourth axis and the second blade about a fifth axis. In some embodiments, a method of performing an operation, e.g. a spinal operation, on a patient using the disclosed retractor is provided.

20 Claims, 22 Drawing Sheets

Related U.S. Application Data

(60) Provisional application No. 62/306,010, filed on Mar. 9, 2016.

(58) Field of Classification Search
CPC .... A61B 17/02; A61B 17/0218; A61B 5/4893
See application file for complete search history.

(56) References Cited

U.S. PATENT DOCUMENTS

| | | | |
|---|---|---|---|
| 1,311,313 A | 7/1919 | Brix | |
| 1,328,624 A | 1/1920 | Graham | |
| 1,613,141 A | 1/1927 | Stein | |
| 1,822,280 A | 9/1931 | Ervay | |
| 2,002,021 A | 5/1935 | Rouse | |
| 2,670,731 A | 3/1954 | Zoll et al. | |
| 2,693,795 A | 11/1954 | Grieshaber | |
| 2,850,008 A | 9/1958 | Resch | |
| 3,168,093 A | 2/1965 | Gauthier | |
| 3,384,078 A | 5/1968 | Gauthier | |
| 3,522,799 A | 8/1970 | Gauthier | |
| 3,747,592 A | 7/1973 | Santos | |
| 3,782,370 A | 1/1974 | McDonald | |
| 3,965,890 A | 6/1976 | Gauthier | |
| 4,156,424 A | 5/1979 | Burgin | |
| 4,616,635 A | 10/1986 | Caspar et al. | |
| 4,667,657 A | 5/1987 | Kulik et al. | |
| 5,035,232 A | 7/1991 | Lutze et al. | |
| 5,113,846 A | 5/1992 | Hiltebrandt et al. | |
| 5,363,841 A | 11/1994 | Coker | |
| 5,618,260 A | 4/1997 | Caspar et al. | |
| 5,681,265 A | 10/1997 | Maeda et al. | |
| 5,772,583 A | 6/1998 | Wright et al. | |
| 5,928,139 A | 7/1999 | Koros et al. | |
| 5,931,777 A | 8/1999 | Sava | |
| 5,931,778 A | 8/1999 | Furnish | |
| 5,980,455 A | 11/1999 | Daniel et al. | |
| 6,042,540 A | 3/2000 | Johnston et al. | |
| 6,074,343 A | 6/2000 | Nathanson et al. | |
| 6,080,155 A | 6/2000 | Michelson | |
| 6,139,493 A | 10/2000 | Koros et al. | |
| 6,206,826 B1 | 3/2001 | Mathews et al. | |
| 6,264,650 B1 | 7/2001 | Hovda et al. | |
| 7,087,055 B2 | 8/2006 | Lim et al. | |
| 7,229,408 B2 | 6/2007 | Douglas et al. | |
| 7,390,298 B2 | 6/2008 | Chu | |
| 7,481,766 B2 | 1/2009 | Lee et al. | |
| 7,491,168 B2 | 2/2009 | Raymond et al. | |
| 7,537,565 B2 | 5/2009 | Bass | |
| 7,582,058 B1 * | 9/2009 | Miles | A61B 17/0293 607/2 |
| 7,594,888 B2 | 9/2009 | Raymond et al. | |
| 7,691,057 B2 * | 4/2010 | Miles | A61B 1/32 600/210 |
| 7,722,613 B2 | 5/2010 | Sutterlin et al. | |
| 7,785,253 B1 | 8/2010 | Arambula et al. | |
| 7,819,801 B2 | 10/2010 | Miles et al. | |
| 7,846,183 B2 | 12/2010 | Blain | |
| 7,892,173 B2 | 2/2011 | Miles et al. | |
| 7,905,840 B2 * | 3/2011 | Pimenta | A61B 17/02 |
| 7,922,658 B2 | 4/2011 | Cohen et al. | |
| 8,062,217 B2 | 11/2011 | Boucher et al. | |
| 8,062,218 B2 | 11/2011 | Sebastian et al. | |
| 8,137,284 B2 | 3/2012 | Miles et al. | |
| 8,142,355 B2 | 3/2012 | Blain et al. | |
| 8,192,356 B2 | 6/2012 | Miles et al. | |
| 8,303,498 B2 | 11/2012 | Miles et al. | |
| 8,303,515 B2 | 11/2012 | Miles et al. | |
| 8,313,430 B1 * | 11/2012 | Pimenta | A61B 17/0206 600/202 |
| 8,353,826 B2 | 1/2013 | Weiman | |
| 8,388,527 B2 | 3/2013 | Miles et al. | |
| 8,409,091 B2 | 4/2013 | Blain et al. | |
| 8,500,634 B2 | 8/2013 | Miles et al. | |
| 8,523,768 B2 | 9/2013 | Miles et al. | |
| 8,556,808 B2 | 10/2013 | Miles et al. | |
| 8,628,469 B2 | 1/2014 | Miles et al. | |
| 8,663,102 B2 | 3/2014 | Michaeli et al. | |
| 8,740,786 B2 | 6/2014 | Blain et al. | |
| 8,753,270 B2 | 6/2014 | Miles et al. | |
| 8,753,271 B1 | 6/2014 | Miles et al. | |
| 8,821,396 B1 | 9/2014 | Miles et al. | |
| 8,876,687 B2 | 11/2014 | Jones et al. | |
| 8,876,904 B2 * | 11/2014 | Pimenta | A61N 1/36017 606/210 |
| 8,915,846 B2 | 12/2014 | Miles et al. | |
| 8,945,004 B2 | 2/2015 | Miles et al. | |
| 8,986,344 B2 | 3/2015 | Sandhu | |
| 9,028,522 B1 * | 5/2015 | Prado | A61B 17/0206 606/191 |
| 9,044,280 B1 | 6/2015 | Arambula et al. | |
| 9,050,146 B2 | 6/2015 | Woolley et al. | |
| 9,066,701 B1 * | 6/2015 | Finley | A61B 90/30 |
| 9,138,217 B2 * | 9/2015 | Smith | A61B 17/0206 |
| 9,220,491 B2 | 12/2015 | Nunley et al. | |
| 9,265,490 B2 * | 2/2016 | Bowman | A61B 17/025 |
| 9,351,718 B1 | 5/2016 | Arambula et al. | |
| 9,387,009 B2 * | 7/2016 | Fatone | A61B 17/3423 |
| 9,408,596 B2 | 8/2016 | Blain | |
| 9,414,831 B2 | 8/2016 | Sandhu | |
| 9,451,940 B2 | 9/2016 | Spann | |
| 9,456,846 B2 | 10/2016 | Predick | |
| 9,468,405 B2 | 10/2016 | Miles et al. | |
| 9,486,133 B2 * | 11/2016 | Lee | A61B 17/02 |
| 9,572,560 B2 * | 2/2017 | Mast | A61B 17/025 |
| 9,585,649 B2 | 3/2017 | Blain et al. | |
| 9,610,071 B2 | 4/2017 | Miles et al. | |
| 9,615,818 B2 | 4/2017 | Baudouin et al. | |
| 9,622,732 B2 | 4/2017 | Martinelli et al. | |
| 9,649,101 B2 | 5/2017 | Karpowicz et al. | |
| 9,693,761 B2 | 7/2017 | Fedorov et al. | |
| 9,693,762 B2 | 7/2017 | Reimels | |
| 9,693,763 B2 | 7/2017 | Blain | |
| 9,737,288 B2 | 8/2017 | Karpowicz et al. | |
| 9,750,490 B2 | 9/2017 | Miles et al. | |
| 9,782,158 B2 | 10/2017 | Nunley et al. | |
| 9,788,822 B2 | 10/2017 | Miles et al. | |
| 9,795,371 B2 | 10/2017 | Miles et al. | |
| 9,820,729 B2 | 11/2017 | Miles et al. | |
| 9,826,966 B2 | 11/2017 | Mast et al. | |
| 9,826,968 B2 | 11/2017 | Miles et al. | |
| 9,833,227 B2 | 12/2017 | Miles et al. | |
| 9,848,863 B2 | 12/2017 | Cryder et al. | |
| 9,861,273 B2 | 1/2018 | Weiman | |
| 9,943,301 B2 | 4/2018 | Mast et al. | |
| 10,039,539 B2 | 8/2018 | Friedrich et al. | |
| 10,076,320 B2 | 9/2018 | Mast et al. | |
| 10,085,854 B2 | 10/2018 | Spann | |
| 10,166,018 B2 * | 1/2019 | Hunt | A61B 17/282 |
| 10,172,603 B2 | 1/2019 | Blain | |
| 10,178,987 B2 | 1/2019 | Predick | |
| 10,299,777 B2 | 5/2019 | Mast et al. | |
| 10,383,613 B2 | 8/2019 | Daavettila et al. | |
| 10,426,450 B2 | 10/2019 | Vogel et al. | |
| 10,532,197 B2 * | 1/2020 | Predick | A61M 29/00 |
| D882,781 S | 4/2020 | Rustamzadeh | |
| 10,898,174 B2 | 1/2021 | Blain | |
| 10,945,861 B2 | 3/2021 | Abdou | |
| 10,973,505 B2 | 4/2021 | Ortiz et al. | |
| 11,179,146 B2 | 11/2021 | Vogel et al. | |
| D956,224 S | 6/2022 | Gregersen et al. | |
| D956,225 S | 6/2022 | Gregersen et al. | |
| 11,589,858 B2 | 2/2023 | Berry | |
| 11,801,042 B2 | 10/2023 | Blain | |
| 2002/0123668 A1 | 9/2002 | Ritland | |
| 2005/0102029 A1 | 5/2005 | Blain | |
| 2005/0107877 A1 | 5/2005 | Blain | |
| 2005/0159650 A1 | 7/2005 | Raymond et al. | |
| 2005/0159651 A1 | 7/2005 | Raymond et al. | |
| 2005/0159818 A1 | 7/2005 | Blain | |
| 2005/0192574 A1 | 9/2005 | Blain | |
| 2006/0004261 A1 | 1/2006 | Douglas | |
| 2006/0074278 A1 | 4/2006 | Petit et al. | |
| 2006/0074425 A1 | 4/2006 | Sutterlin et al. | |
| 2006/0106416 A1 | 5/2006 | Raymond et al. | |

(56) References Cited

U.S. PATENT DOCUMENTS

| | | |
|---|---|---|
| 2006/0224044 A1 | 10/2006 | Marchek et al. |
| 2006/0235423 A1 | 10/2006 | Cantu |
| 2007/0073111 A1 | 3/2007 | Bass |
| 2007/0100212 A1 | 5/2007 | Pimenta et al. |
| 2007/0185376 A1 | 8/2007 | Wilson et al. |
| 2007/0238932 A1 | 10/2007 | Jones et al. |
| 2008/0097164 A1 | 4/2008 | Miles et al. |
| 2008/0114208 A1 | 5/2008 | Hutton et al. |
| 2008/0132766 A1 | 6/2008 | Dant et al. |
| 2008/0188718 A1 | 8/2008 | Spitler et al. |
| 2009/0018399 A1 | 1/2009 | Martinelli |
| 2009/0048668 A1 | 2/2009 | Wilson et al. |
| 2009/0259108 A1 | 10/2009 | Miles et al. |
| 2010/0114110 A1 | 5/2010 | Taft et al. |
| 2010/0174146 A1 | 7/2010 | Miles et al. |
| 2011/0034777 A1 | 2/2011 | Ames et al. |
| 2011/0130793 A1 | 6/2011 | Woolley et al. |
| 2011/0208226 A1 | 8/2011 | Fatone |
| 2011/0224497 A1 | 9/2011 | Weiman et al. |
| 2012/0191003 A1 | 7/2012 | Garabedian |
| 2012/0245431 A1* | 9/2012 | Baudouin ............ A61B 17/0293 600/219 |
| 2012/0245432 A1 | 9/2012 | Karpowicz et al. |
| 2013/0158359 A1 | 6/2013 | Predick et al. |
| 2013/0190575 A1* | 7/2013 | Mast .................. A61B 17/7079 600/219 |
| 2013/0261401 A1 | 10/2013 | Hawkins et al. |
| 2013/0274557 A1* | 10/2013 | Bowman ............ A61B 17/0206 600/208 |
| 2014/0024900 A1 | 1/2014 | Capote et al. |
| 2014/0135584 A1 | 5/2014 | Lee et al. |
| 2014/0148652 A1 | 5/2014 | Weiman |
| 2014/0172002 A1* | 6/2014 | Predick ................ A61B 17/025 606/191 |
| 2014/0257035 A1 | 9/2014 | Blain |
| 2015/0051448 A1 | 2/2015 | Hunt |
| 2015/0088030 A1 | 3/2015 | Taylor |
| 2015/0230787 A1 | 8/2015 | Friedrich et al. |
| 2015/0250466 A1 | 9/2015 | Thornburg |
| 2015/0250467 A1 | 9/2015 | Higgins |
| 2015/0265265 A1 | 9/2015 | Hynes |
| 2016/0030030 A1 | 2/2016 | Bass |
| 2016/0317137 A1 | 11/2016 | Predick et al. |
| 2017/0231614 A1 | 8/2017 | Vogel |
| 2017/0281039 A1 | 10/2017 | Blain |
| 2019/0110785 A1 | 4/2019 | Serokosz et al. |
| 2019/0125328 A1 | 5/2019 | Blain |
| 2019/0350573 A1 | 11/2019 | Vogel et al. |
| 2021/0015514 A1 | 1/2021 | Storli et al. |
| 2021/0085306 A1 | 3/2021 | Clauss et al. |
| 2021/0169463 A1 | 6/2021 | Blain |
| 2022/0079573 A1 | 3/2022 | Ortiz et al. |
| 2022/0096072 A1 | 3/2022 | Vogel et al. |
| 2022/0289135 A1 | 9/2022 | Moon et al. |
| 2024/0008863 A1 | 1/2024 | Vidmar et al. |
| 2024/0156448 A1 | 5/2024 | Blain |

FOREIGN PATENT DOCUMENTS

| | | |
|---|---|---|
| JP | 2013-521896 | 6/2013 |
| JP | 2013-537467 | 10/2013 |
| JP | 2014-515646 | 7/2014 |
| WO | WO 2006/042241 | 4/2006 |
| WO | WO 2012/026981 | 3/2012 |
| WO | WO 2012/040206 | 3/2012 |
| WO | WO 2013/028571 | 2/2013 |
| WO | WO 2013/033630 | 3/2013 |
| WO | WO 2015/191836 | 12/2015 |
| WO | WO 2016/040497 | 3/2016 |
| WO | WO 2017/155718 | 9/2017 |

OTHER PUBLICATIONS

Official Communication in Japanese Application No. 2017-513531, dated May 25, 2020.
Official Communication in Japanese Application No. 2017-513531, dated Feb. 22, 2021.
Official Communication in European Application No. 17763744.4, dated Nov. 12, 2019.
International Search Report and Written Opinion in International Application No. PCT/US2020/051031, dated Dec. 8, 2020.
Official Communication in Australian Application No. 2015315166, dated Apr. 24, 2019.
Official Communication in Australian Application No. 2015315166, dated Aug. 15, 2019.
Official Communication in European Application No. 15840714.8, dated Feb. 12, 2018.
Official Communication in Japanese Application No. 2017-513531, dated Jun. 24, 2019.
International Search Report and Written Opinion in International Application No. PCT/US2015/049211, dated Dec. 4, 2015.
International Preliminary Report on Patentability and Written Opinion in International Application No. PCT/US2015/049211, dated Mar. 23, 2017.
Invitation to Pay Additional Search Fees in International Application No. PCT/US2017/019699, dated May 24, 2017.
International Search Report and Written Opinion in International Application No. PCT/US2017/019699, dated Aug. 7, 2017.
International Preliminary Report on Patentability and Written Opinion in International Application No. PCT/US2017/019699, dated Sep. 20, 2018.
Dimension®, MIS TLIF Retractor System, Spinal Elements, https://spinalelements.com/products/access-systems/dimension/, 2023, pp. 1.
Official Communication in Australian Application No. 2020203261, dated Jul. 26, 2021.
Official Communication in Australian Application No. 2020203261, dated May 6, 2022.
Official Communication in Canadian Application No. 2,960,818, dated May 3, 2021.
Official Communication in Japanese Application No. 2017-513531, dated Sep. 6, 2021.
Official Communication in Japanese Application No. 2021-164806, dated Dec. 23, 2022.
Official Communication in Australian Application No. 2017228829, dated May 17, 2021.
Official Communication in Australian Application No. 2017228829, dated Feb. 23, 2022.
Official Communication in Canadian Application No. 3,015,212, dated Apr. 4, 2023.
International Preliminary Report on Patentability and Written Opinion in International Application No. PCT/US2020/051031, dated Mar. 31, 2022.

* cited by examiner

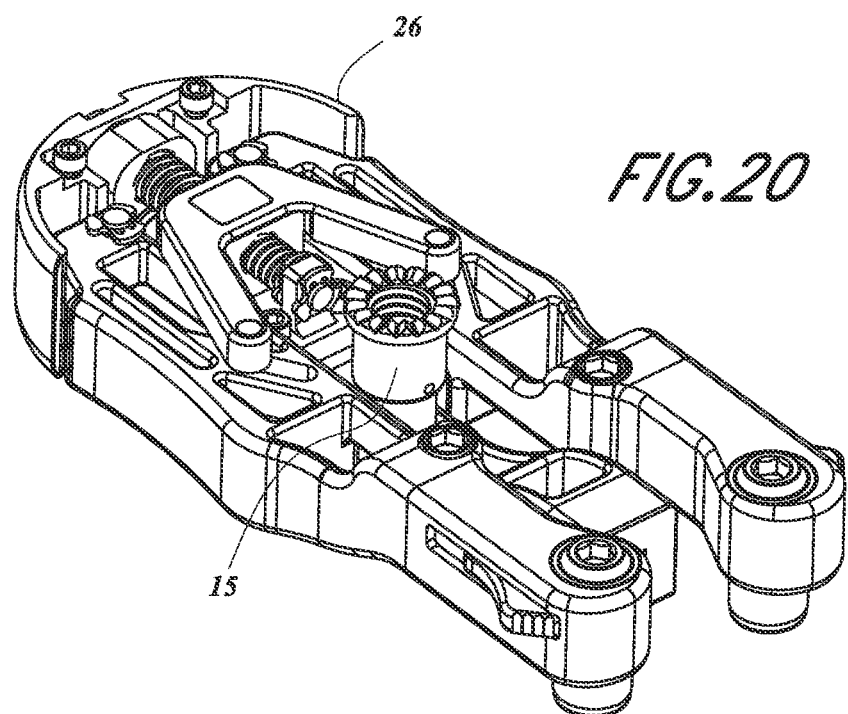

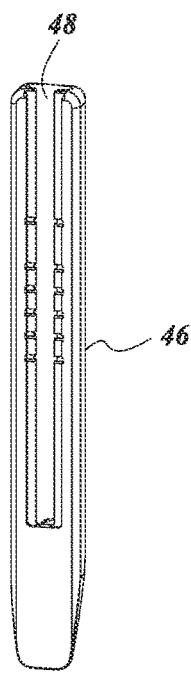
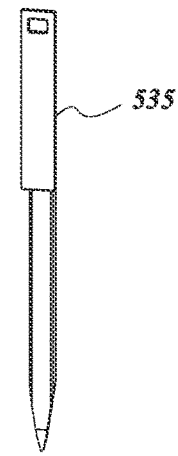
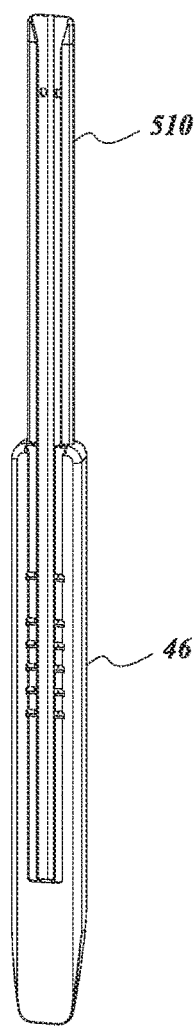
FIG.21C          FIG.21D

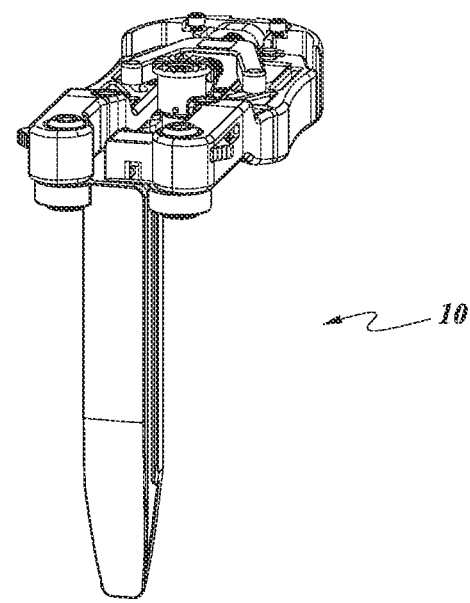
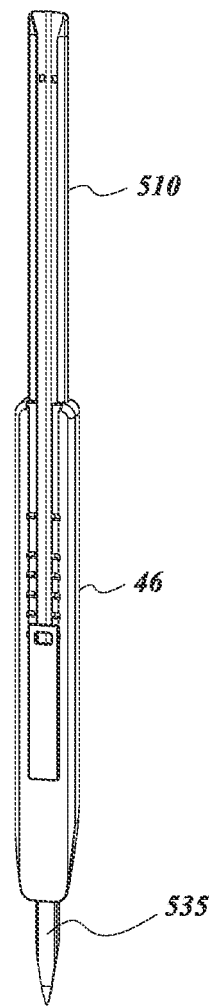
FIG.21E

RETRACTOR

CROSS-REFERENCE TO RELATED APPLICATIONS

This application is a continuation of U.S. patent application Ser. No. 16/082,797, filed Sep. 6, 2018, which is the U.S. National Phase under 35 U.S.C. § 371 of International Application No. PCT/US2017/019699, filed Feb. 27, 2017 titled RETRACTOR, which claims priority benefit to U.S. Provisional Patent Application No. 62/306,010, filed Mar. 9, 2016, which are hereby incorporated by reference herein in their entirety. This application is related to PCT/US2015/049211, filed Sep. 9, 2015 and U.S. Provisional Patent Application No. 62/048,639, filed Sep. 10, 2014, the disclosures of each are incorporated by reference herein in their entireties.

FIELD

The present application relates to surgical methods and tools, and more particularly to a retractor and a method of operating a retractor.

BACKGROUND

Retractors are surgical devices used to spread bodily tissues in order to allow a surgeon or surgical assistant to see and access a part of the body that is to be surgically treated. In general, retractors comprise a pair of jaws or blades that grip the bodily tissue and push it apart under the force generated by an actuator, such as a pair of scissor-like arms having a distal end and a proximal end. The proximal end generally defines a pair of handles and the distal end attaches to the pair of blades so that manipulation of the handles causes the blades to move apart from one another. Once an incision is made in the body to be operated on, the blades are inserted into the incision and the actuator is manipulated to move the blades of the retractor apart, thus spreading the tissue and providing an aperture through which the surgeon can access visualize the tissue to be surgically treated. One problem with this type of retractor is that the aperture size is generally limited by the size of the incision, meaning that a large aperture requires a relatively large incision. The drawback to this arrangement is that larger incisions result in the need for longer periods for healing of the incision. There is thus a need for a surgical retractor that is capable of creating a relatively large aperture using a relatively small incision, thereby reducing the invasiveness of the surgical procedure, post-operative healing times and patient discomfort.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

These and other features, aspects and advantages of the described embodiments are described with reference to drawings of certain preferred embodiments, which are intended to illustrate, but not to limit. It is to be understood that the attached drawings are for the purpose of illustrating concepts of the described embodiments and may not be to scale.

FIG. 20 provides a perspective view of an attachment mechanism of FIG. 1.

FIGS. 21A-E show the use of a probe system to insert the retractor of FIG. 1 to form an operative channel through the tissue of a patient to access a portion of the patient's spine.

DETAILED DESCRIPTION

Figure 1:
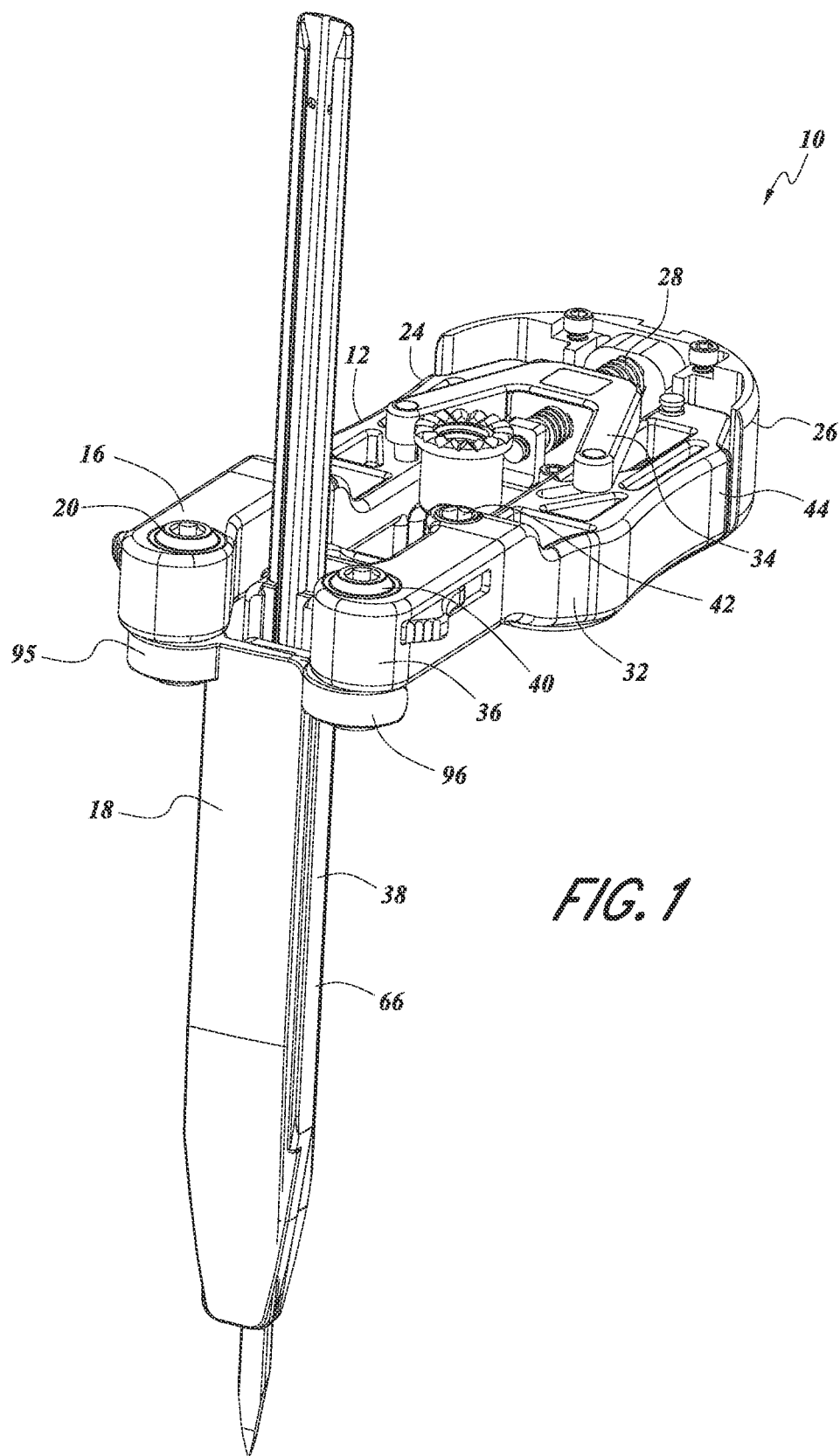
FIG. 1 provides a perspective view of an embodiment of a retractor with the blades in a closed position.

As will be explained below, certain retractor embodiments described herein provide advantages over the prior art retractors comprising a set of blades and an actuator, such as a set of scissor arms. For example, the retractor of the illustrated embodiment allows a person to insert a relatively compact set of retractor blades into an incision having a short length. In some embodiments, the compact set of retractor blades (e.g., a first blade, a second blade, a third blade) are of such a size that they can be inserted within the incision so that they are snugly embraced by the side walls of the incision (e.g., a closed position).

Optionally, an actuator causes the first blade and the second blade to move apart (e.g., to an opened position) in a direction that can be essentially parallel to the length of the incision. This can cause the tissue to stretch in one direction (e.g., along the length of the incision), creating an opening having a length in that direction that is substantially longer than the incision. Once the retractor is opened in the first direction, the actuator may be locked open. Optionally, a rotation mechanism on the first and/or second blades may be manipulated to rotate the blades (e.g., to a rotated position), for example, pulling the incised tissue apart in one or more directions that are not parallel to the incision. Optionally, a pivot mechanism on the first and/or second blades can be manipulated to pivot the blades (e.g., to a pivoted position), pulling the incised tissue apart in one or more directions that are not parallel to the incision. Optionally, an adjuster on the first and/or second arms can be manipulated to slide or otherwise translate the arms (e.g., to a slid position), pulling the incised tissue apart in directions that are not parallel to the incision. Optionally, an adjuster on the third blade can be manipulated to slide or otherwise translate the third blade (e.g., to a slid position), pulling the incised tissue apart in directions that are not parallel to the incision. In some embodiments, these directions may be perpendicular, substantially perpendicular or oblique to the incision. In certain embodiments, the retractor can be used to open up an aperture that is substantially longer and/or wider than the incision, and is substantially larger than would be possible using a prior art device and/or in a manner that is easier to use and/or requiring less steps and/or less complicated steps. In certain arrangements in relative terms, the surgeon can use a smaller incision, and in some cases a much smaller incision, than would have been required with a prior art device. Moreover, in certain arrangements, removal of the retractor, e.g. by closing the blades, closing the arms and removing the blades from the incision, can allow the incision to relax back to a size that is much smaller than would have resulted from use of the prior art retractor. In addition, in certain arrangements, steps performed by the surgeon to retract the tissue can be simplified, easier to use and/or involve less steps as compared to prior art devices.

The illustrated embodiment will now be further described with reference to the appended drawings. In FIG. 1 there is shown a perspective view of a retractor 10 having a body 26. The retractor 10 comprises a first arm 12 to which can be coupled a first blade assembly 16 comprising a first blade 18. The first blade assembly 16 can include a first rotation mechanism 20 to rotate the first blade 18. The first blade assembly 16 and the first arm 12 can also include a first pivot mechanism 22 to pivot the first blade 18. The first arm 12 has a proximal end 24 opposite the first blade assembly 16.

The retractor 10 can include a second arm 32 to which can be coupled a second blade assembly 36 comprising a second blade 38. The second blade assembly 36 can include a second rotation mechanism 40 to rotate the second blade 38. The second blade assembly 36 and the second arm 32 can include a second pivot mechanism 42 to pivot the second blade 38. The second arm 32 has a proximal end 44 opposite the second blade assembly 36. The first arm 12 and the second arm 32 can be coupled to a slide mechanism 28 to slide the first arm 12 and the second arm 32 relative to the body 26. The first arm 12 and the second arm 32 can be coupled to a spread mechanism 34 to slide the first arm 12 and the second arm 32 relative to the body 26.

Figure 2:
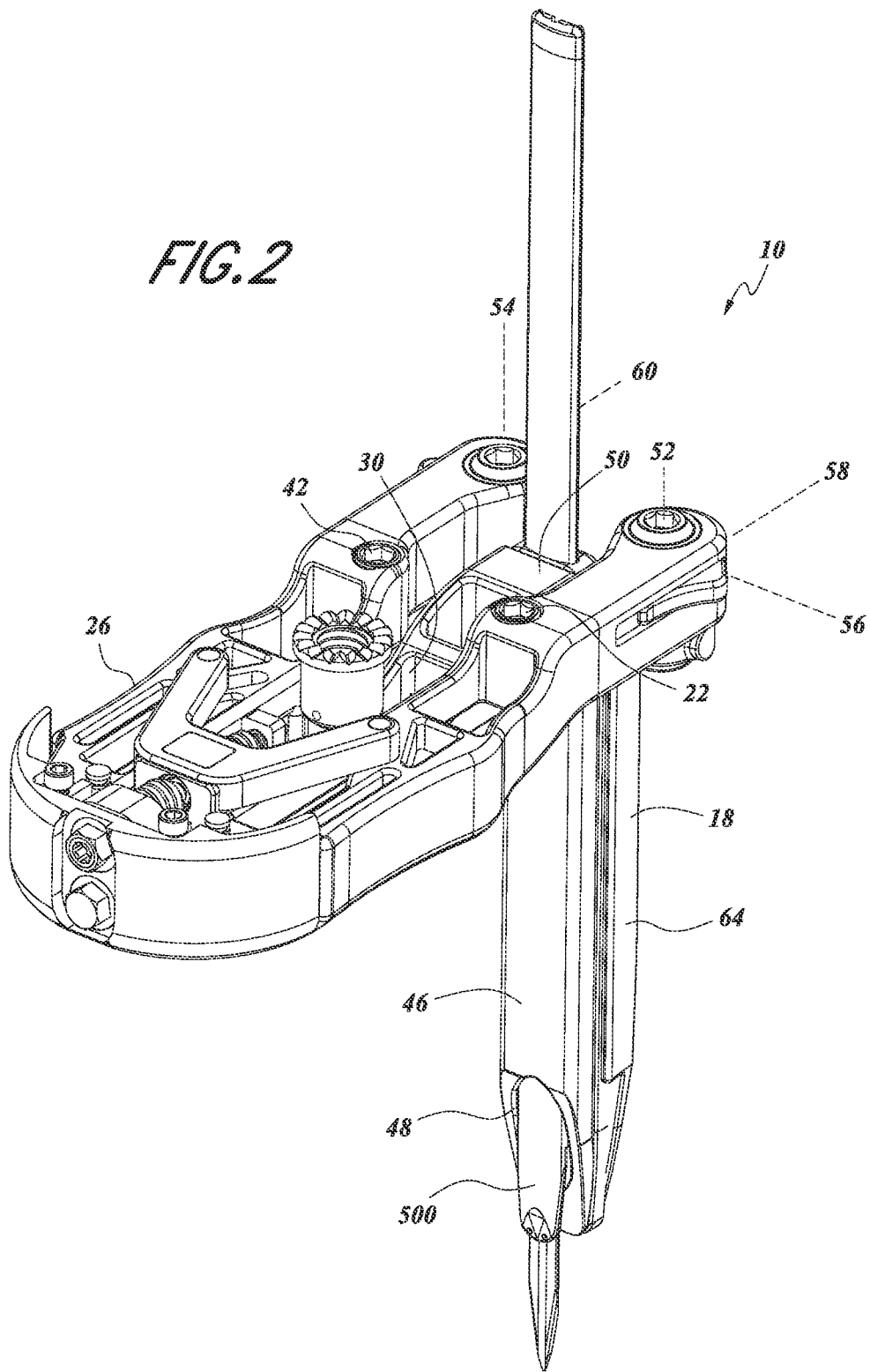
FIG. 2 provides a perspective view of the retractor of FIG. 1 with the blades in a closed position.

In the illustrated embodiment of FIG. 2, the retractor can include a third blade 46 coupled to the third arm 50. The third blade 46 can include a longitudinally extending slot 48 sized to accept a probe system 500, described herein. In the illustrated embodiment, the probe system 500 can be configured to be inserted from the tip of the third blade 46 toward the body 26. Other configurations are contemplated.

The third arm 50 of the third blade 46 can be coupled with the slide mechanism 30 of the body 26 to slide the third blade 46 in relation to the body 26. In the illustrated embodiment, the third blade 46 is configured to be inserted from underneath the body 26. The third arm 50 can interlock to securely couple the third blade 46 to the body 26. In some embodiments, the third arm 50 forms a snap fit. In some embodiments, the third arm 50 makes an audible noise when the third blade 46 is coupled to the body 26. Other configurations for coupling these two components together are contemplated, such as, for example a male/female connection and/or permanently connecting the parts and/or forming the parts out of more or less components.

The first rotation mechanism 20 rotates the first blade 18 about a first axis 52. The second rotation mechanism 40 rotates the second blade 38 about a second axis 54. In the illustrated arrangement, the first axis 52 passes vertically or substantially vertically through the first blade 18, and the second axis passes vertically or substantially vertically through second blade 38. In some embodiments, the first and second axes 52, 54 may be substantially coplanar with one another. Indeed in some embodiments, the first and second axes 52, 54 are not only coplanar but also substantially parallel to one another. In particular embodiments, the first and second axes 52, 54 are coplanar with, parallel to, or at some pre-determined skew angle with respect to one another. As will be described above, various embodiments will be described as "substantially" vertically, parallel, coplanar and/or perpendicular. In such embodiments, "substantially" can mean within plus or minus 25 degrees from the given orientation, in other embodiments, within plus or minus 10 degrees from the given orientation, and in other embodiments, within plus or minus 5 degrees from the given orientation.

In the illustrated embodiment, the first blade assembly 16 and the second blade assembly 36 can translate along a third axis 56 (see e.g., FIG. 3), e.g., spread. The first arm 12 and the second arm 32 can be coupled to a spread mechanism 34 to spread the first arm 12 and the second arm 32 relative to the body 26. In the illustrated embodiment, the first blade assembly 16 and the second blade assembly 36 can move relative to one another along an arc. In the illustrated embodiment, their general direction of motion relative to one another, and the direction of motion can be along the common third axis 56 that is generally defined by a line passing through the first axis 52 and the second axis 54. In other embodiments, the first blade assembly 16 and the second blade assembly 36 can rotate about different axes (e.g., axes that are parallel to each other or slightly skewed). In some examples, the third axis 56 is perpendicular or substantially perpendicular to the first axis 52, the second axis 54 or both the first and second axes 52, 54. In particular embodiments, the third axis 56 is substantially perpendicular or perpendicular to both the first axis 52 and the second axis 54. In some embodiments, the third axis 56 is substantially perpendicular or perpendicular to the first axis 52, the second axis 54 or both the first and second axes 52, 54. In some embodiments, the third axis 56 is perpendicular or substantially perpendicular to both the first and second axes 52, 54. In some embodiments, the retractor 10 described herein possesses a mechanism (e.g., set screw, set pin, clamp, detent, ratchet mechanism etc.) for locking the first blade assembly 16 and the second blade assembly 36 in at least one predetermined position along the third axis 56.

The first pivot mechanism 22 can pivot the first blade 18 about a fourth axis 58. The second pivot mechanism 42 can pivot the second blade 38 about a fifth axis 60. In some such embodiments, the fourth axis 58 and the fifth axis 60 may be substantially coplanar or coplanar with one another. Indeed in some embodiments, the fourth axis 58 and the fifth axis 60 are not only coplanar but also substantially parallel or parallel to one another. In particular embodiments, the fourth axis 58 and the fifth axis 60 are substantially coplanar with, coplanar with, substantially parallel to, parallel to, or at some pre-determined skew angle with respect to one another.

Figure 3:
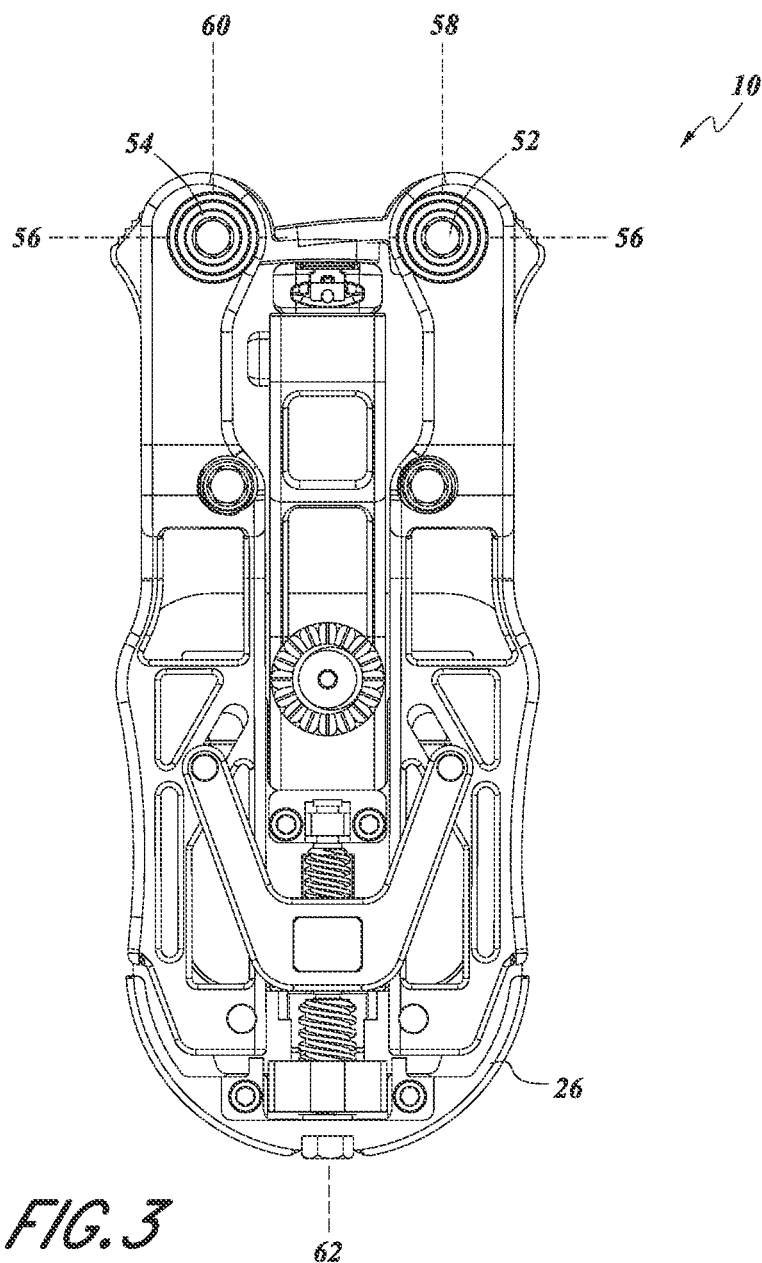
FIG. 3 provides a top view of a retractor of FIG. 1 with the blades in a closed position.

In the illustrated embodiment, the first blade assembly 16 and the second blade assembly 36 can slide along a sixth axis 62 (see e.g., FIG. 3). In the illustrated embodiment, the third blade 46 can slide along the sixth axis 62. In some embodiments, the third blade 46 can slide independently of the first blade assembly 16 and the second blade assembly 36. In the illustrated embodiment, the first blade assembly 16 and the second blade assembly 36 can move together in a proximal-distal direction. In other embodiments, the first blade assembly 16 and the second blade assembly 36 can slide about different axes (e.g., axes that are parallel to each other or slightly skewed). In some examples, the sixth axis 62 is perpendicular or substantially perpendicular to the first axis 52, the second axis 54, or the third axis 56. In particular embodiments, the sixth axis 62 is substantially perpendicular or perpendicular to both the first axis 52 and the second axis 54. In some embodiments, the sixth axis 62 is substantially parallel or parallel to the fourth axis 58, the fifth axis 60 or both the fourth and fifth axes 58, 60. In some embodiments, the retractor 10 described herein possesses a mechanism (e.g., set screw, set pin, clamp, detent, ratchet mechanism etc.) for locking the first blade assembly 16 and the second blade assembly 36 in at least one predetermined position along the sixth axis 62. In some embodiments, the retractor 10 described herein possesses a mechanism (e.g., set screw, set pin, clamp, detent, ratchet mechanism etc.) for locking the third blade 46 in at least one predetermined position along the sixth axis 62. In some embodiments, through all the additional movements about the axes 52, 54, 56, 58, 60, 62 the third blade 46 can remain stationary and fixed relative to the body 26. In other words, during all movement of the first blade 18 and the second blade 38 the third blade 26 can remain immobile. In some embodiments, the third blade 46 can move relative to the first blade assembly 16 and the second blade assembly 36 through all the additional movements of the first blade assembly 16 and the second blade assembly 36 about the axes 52, 54, 56, 58, 60, 62. For example, the third blade 46 can move along the sixth axis 62 while the first blade 18 and the second blade 38 remain stationary. In another example, the third blade 46 can pivot relative to the first blade 18 and the second blade 38. The third blade 46 can be hingedly connected to the body 26 and can pivot toward the proximal direction to help create an enlarged aperture in the incised tissue.

The blades 18, 38, 46 may have a variety of configurations. In some embodiments, at least one blade is substantially flat. In some embodiments (e.g., the illustrated embodiment of FIGS. 1-3), at least one blade is bent or beveled in order to enhance the ability of the blades to lie flat when the blades are in the closed position. This arrangement can allow the first and second blades 18, 38 to exert force on the skin about an incision in opposing directions substantially perpendicular to the blade axes and perpendicular or oblique to a cord defined by the points at which the blade axes intersect the arms 12, 32 of the retractor 10. In some embodiments, one or more blades 18, 38, 46 can be fan shaped.

In some embodiments, two of the blades are of substantially different sizes in at least one dimension. In some embodiments, the at least two blades of different sizes are the first blade 18 and second blade 38. In some embodiments, the at least two blades of different sizes are the first blade 18 and the third blade 46. In some embodiments, the at least two blades of different sizes are the second blade 38 and the third blade 46. In some embodiments, at least one of the blades 18, 38, 46 is a comb-shaped blade. In some embodiments, at least one of the blades 18, 38, 46 is a substantially flat blade. In some embodiments, the retractor 10 can include at least one removable blade. In some embodiments, the first blade 18 and the second blade 38 are removable. In some embodiments, the first blade assembly 16 and the second blade assembly 36 are removable. In some embodiments, the third blade 46 is removable. The first blade 18 can include a first bridge 95 and the second blade 38 can include a second bridge 96. The blades 18, 38 can have a variety of lengths of bridges 95, 96. The bridges 95, 96 can allow the blade 18, 38 to be smaller than the length of the retractor 10.

The blade assemblies 16, 36 can be removed from the arms 12, 32. In some arrangement, it can be convenient to remove the blade assemblies 16, 36 in order to expedite sterilization of the blade assemblies 16, 36 and/or in order to exchange one or both blade assemblies 16, 36 for other blade assemblies (e.g. blade assemblies with different size blades, different configuration of blades, etc.) as discussed in more detail herein.

In FIGS. 1-3, the retractor 10 is shown in the "closed position," meaning that the first blade 18, the second blade 38, and the third blade 46 are aligned and relatively close to one another so as to provide a smaller cross-sectional area as compared to an "opened position". While the application uses the phrase "the closed position," it is understood that one or more positions may be described as closed. For instance, the blades 18, 38, 46 may be aligned, substantially aligned, stacked, substantially stacked, close together, relatively close together, the first blade 18 encloses the second blade 38, the second blade encloses the third blade 46, the first blade 18 encloses the third blade 46, one or more blades 18, 38, 46 enclose the probe system 500, or any other closed positions.

The first blade 18, the second blade 38, and the third blade 46 can be substantially parallel or parallel in the closed position. The longitudinal axes of the first blade 18, the second blade 38, and the third blade 46 can be aligned on substantially the same or the same plane in the closed position. The length of the three blades 18, 38, 46 in this configuration can be approximately equal to the length of one blade, such as the length of the first blade 18. The first blade 18, the second blade 38, and the third blade 46 can have a stacked configuration. The first blade 18 can be in front (e.g., distal), the second blade 38 can be in the middle, and the third blade 46 can be in back (e.g., proximal).

The first blade 18 can have a first rail 64 that aligns one side of the blades 18, 38, 46. The first rail 64 can extend from the proximal surface of the first blade 18 toward the body 26. The second blade 38 can have a second rail 66 that can extend from both distal surface and the proximal surface of the second blade 38. When viewed from the distal end of the retractor 10 (as shown in FIG. 1), the first rail 64 can extend on the left side of the first blade 18 and the second rail 66 can extend on the right side of the second blade 38. This configuration permits the first blade 18 to slide relative to the second blade 38 without interference of the rails 66, 68. The rails 66, 68 can have a width equal to the width of the stacked blades 18, 38, 46.

In FIGS. 4-9, the retractor 10 is shown in an "opened position," meaning that the first blade 18 can be translated relative to the third blade 46 or the second blade 38 can be translated relative to the third blade 46. The first blade 18 is moved apart from the second blade 38, while the third blade 46 can remain stationary. The first blade 18, the second blade 38, and the third blade 46 can have an overlapped configuration in the opened position, as shown. While the application uses the phrase "the opened position," it is understood that one or more positions may be described as opened. For instance, the blades 18, 38 may be slightly spaced apart, greatly spaced apart, overlapping, not overlapping, adjacent, with a gap between, without a gap between, at any spaced apart location along the third axis 56, wherein the total length in the opened position is greater than the incision length L, or any other opened positions.

The motion of the first blade 18 can be coupled to the motion of the second blade 38 such that actuation of a single actuator such as the spread mechanism 34 that moves both the first blade 18 and the second blade 38 along the third axis 56. In other embodiments, each of the first blade 18 and the second blade 38 is separately actuated. The first blade 18 can be in front (e.g., distal), the second blade 38 can be in the middle, and the third blade 46 can be in back (e.g., proximal). The length L' of the three blades 18, 38, 46 in this configuration is greater than the length L of one blade, such as the length of the first blade 18. When viewed from the distal end of the retractor 10 (shown in FIG. 4). The first blade 18 can translate a first distance to the left of the third blade 46. The second blade 38 can translate a second distance to the right of the third blade 46. The first distance can be equal to the second distance, but need not be. The configuration of the rails 66, 68 permits the first blade 18 to translate relative to the second blade 38 without interference of the rails 66, 68.

Figure 5:
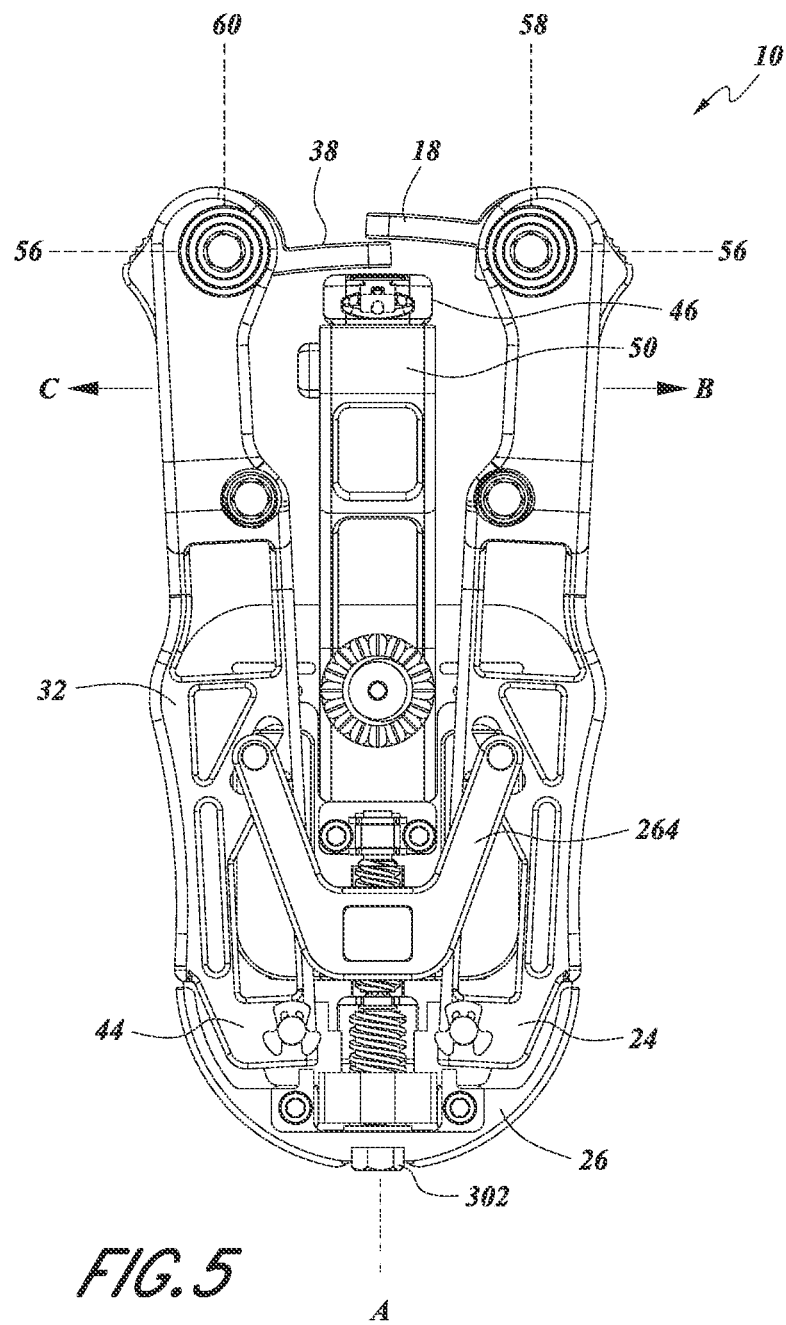
FIG. 5 provides a top view of a retractor of FIG. 4 with the blades in an opened position.
Figure 10:
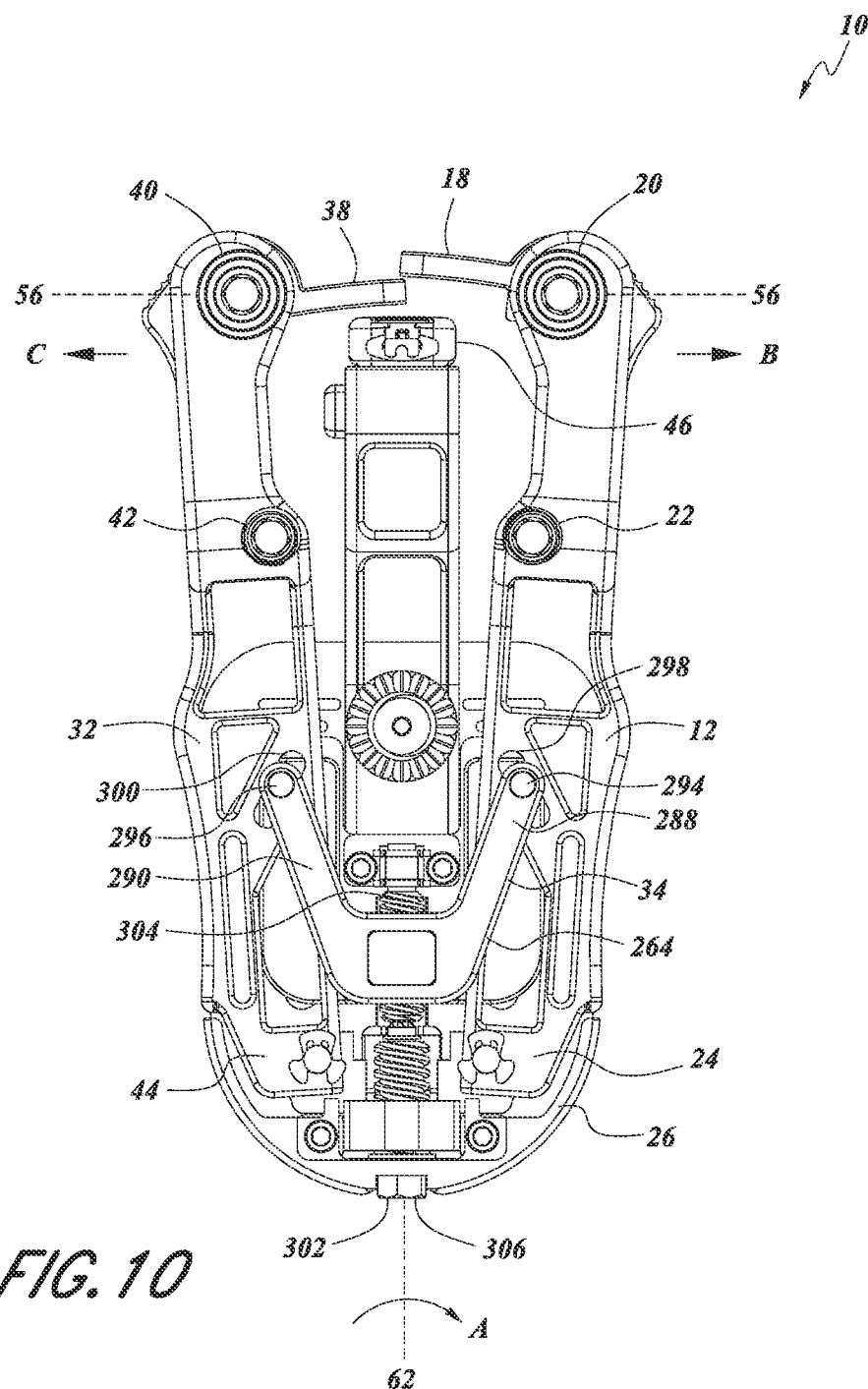
FIG. 10 provides a top view of the retractor of FIG. 1.

FIG. 5 shows the top view of the retractor 10. The retractor 10 can include an actuator 302. The actuator 302 interacts with the arms 12, 32 to spread the arms 12, 32. One embodiment of the actuator is shown in FIG. 10. Rotation of the actuator 302, in the direction of the arrow A in FIG. 10 results in the arms 12, 32 and therefore the blade assemblies 16, 36 moving apart along the directional arrows B and C, causing retractor 10 to assume the opened position depicted in FIG. 5. In the illustrated embodiment, the third axis 56 forms an arc. The first blade 18 will follow an arced path away from the third blade 46. The second blade 38 will follow an arced path away from the third blade 46. The first blade 18 will follow an arced path in separating from the second blade 38. In the illustrated embodiment, the third axis 56 can be substantially perpendicular or perpendicular to the first axis 52 and the second axis 54. The third axis 56 can extend perpendicularly or substantially perpendicularly through the first axis 52 and the second axis 54.

It is noted that in the embodiment depicted in FIG. 5, the retractor 10 comprises a pair of arms 12 and 32 connected via a carriage 264. Other embodiments of an actuator may be used. For example, scissor-like actuators are known in the clamp and retractor arts. In some such embodiments, the actuator comprises a pair of handles (not shown) coupled to the arms 12 and 32. The handles can be roughly parallel and joined together at a pivot point. The handles can be crossed (e.g. scissor-like) handles and joined together at a pivot point. It is also to be understood that when the actuator is a scissor-like embodiment, the motion of blade assemblies 16 and 36 traverse an arc rather than a straight line upon opening of the retractor 10. Nevertheless, the spatial relationship of the two blade assemblies 16 and 36 can be conceptualized as changing along a line described by arrows B and C, which for the purpose of brevity is referred to herein as an axis, and in particular the third axis 56.

While the illustrated embodiment uses a mechanism for moving the first blade 18 and the second blade 38 comprising a pair of arms 12, 32 joined to the carriage 264, other configurations are contemplated. In some embodiments, the proximal ends 24, 44 of the arms 12, 32 can be joined in alternative ways to the body 26 such that the movement of the arms 12, 32 is not a pivoting motion. For instance, arms 12, 32 can be joined one to another by a cross member (not shown). The cross member holds the arms 12, 32 in parallel and stabilizes the arms 12, 32. One or more arms 12, 32 can be moved along the cross member in order to translate the first blade 18 away from the third blade 46 and to translate the second blade 38 away from the third blade 46. In such configurations, the first arm 12 linearly translates relative to the second arm 32 along the third axis 56. In this embodiment, the third axis 56 defines a geometric line passing through and joining the first axis 52 and the second axis 54. The first blade 18 follows a straight path away from the second blade 38.

In some embodiments, the retractor 10 described herein possesses a device for locking the first blade assembly 16 and the second blade assembly 36 in at least one predetermined position along the third axis 56. The device for locking the blade assemblies 16, 36 can be a ratchet (not shown). The device for locking the blade assemblies 16, 36 can be a detent and recess configuration. The device for locking the blade assemblies 16, 36 can be disposed on the pivot or the cross member (not shown).

Figure 4:
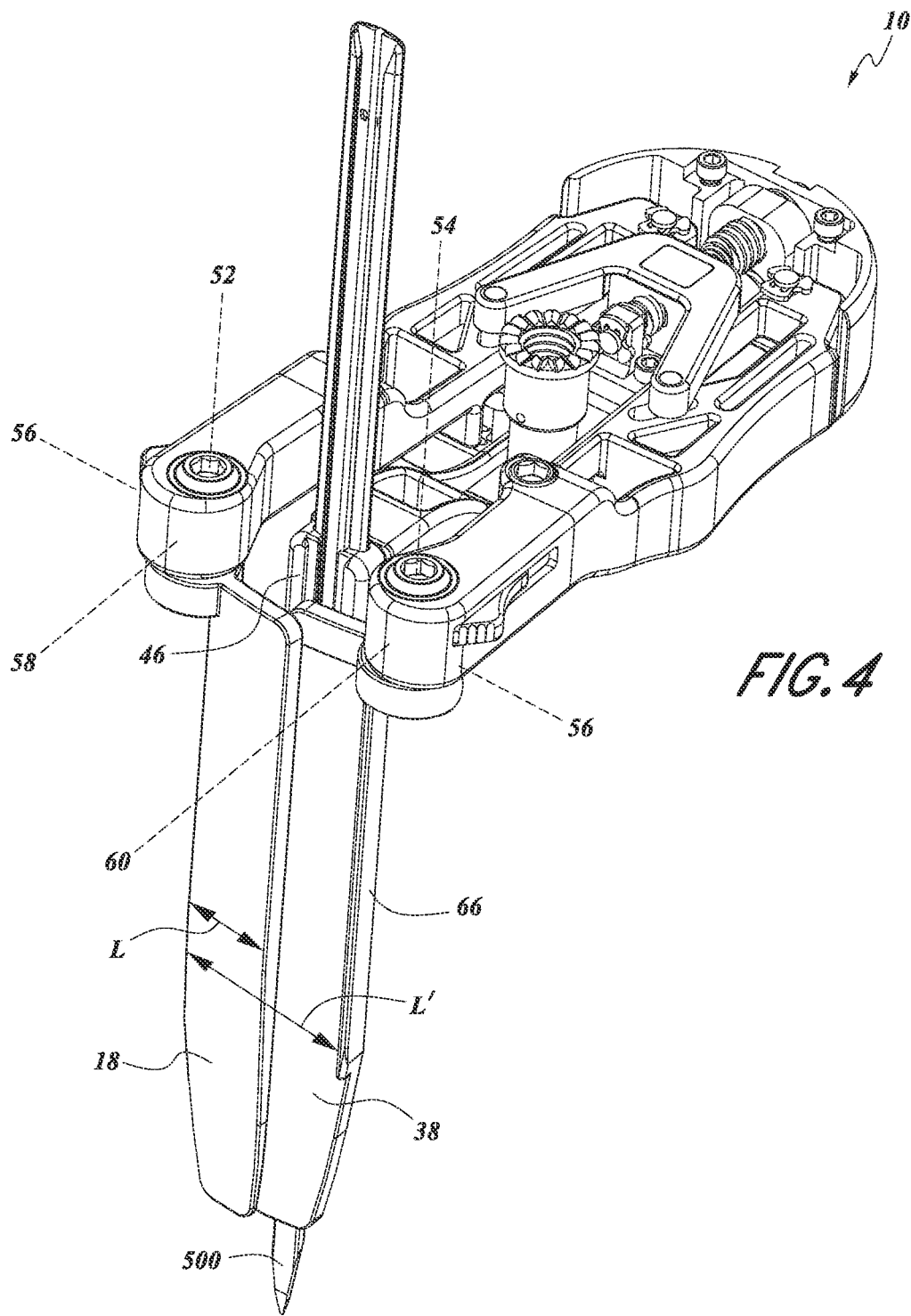
FIG. 4 provides a perspective view of an embodiment of the retractor of FIG. 1, with the blades in an opened position. Opening the retractor along this axis stretches the incision along its length.

Insertion of the blades 18, 38, 46 into an incision in the closed position (as in FIGS. 1-3) and translating the first blade 18 and the second blade 38 to an opened position (such as in FIGS. 4-5) results in a stretching of the incision along the third axis 56. This stretching increases the length of the incision from a length approximately equal to the length L of a single blade (e.g., the first blade 18) to a length L' greater than the length L of a single blade (e.g., the first blade 18). As can be seen in FIGS. 4-5, the retractor 10 is in the opened position, meaning that the first blade 18 is relatively separated from the second blade 38 along the third axis 56. As the blade assembly 16 moves along the directional arrow B and blade assembly 36 moves along the directional arrow C, they exert force in the direction of lines B and C, respectively.

Figure 6:
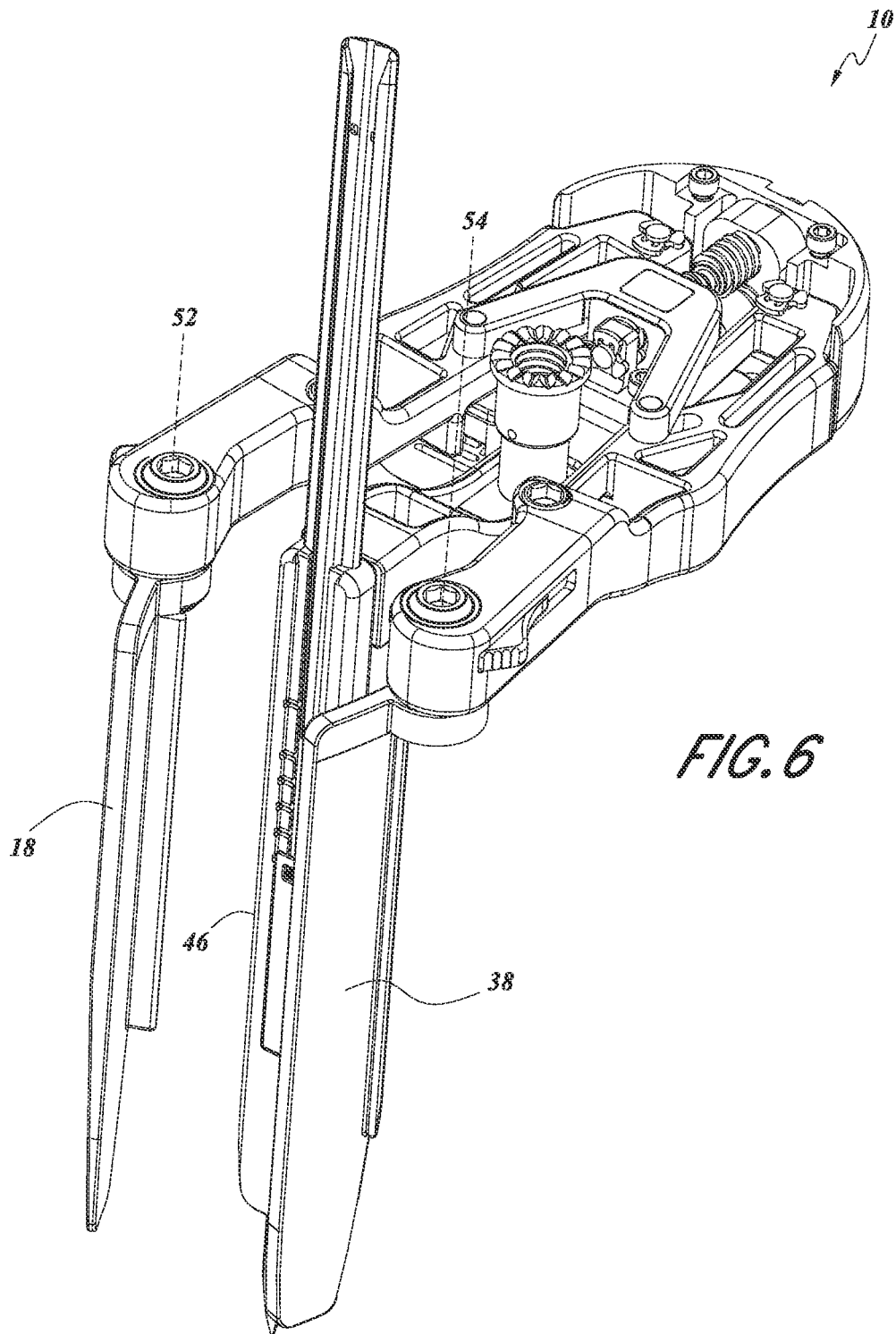
FIG. 6 provides a perspective view of the retractor of FIG. 4 in the rotated position. Opening the retractor along these axes stretches the incision along its width.
Figure 7:
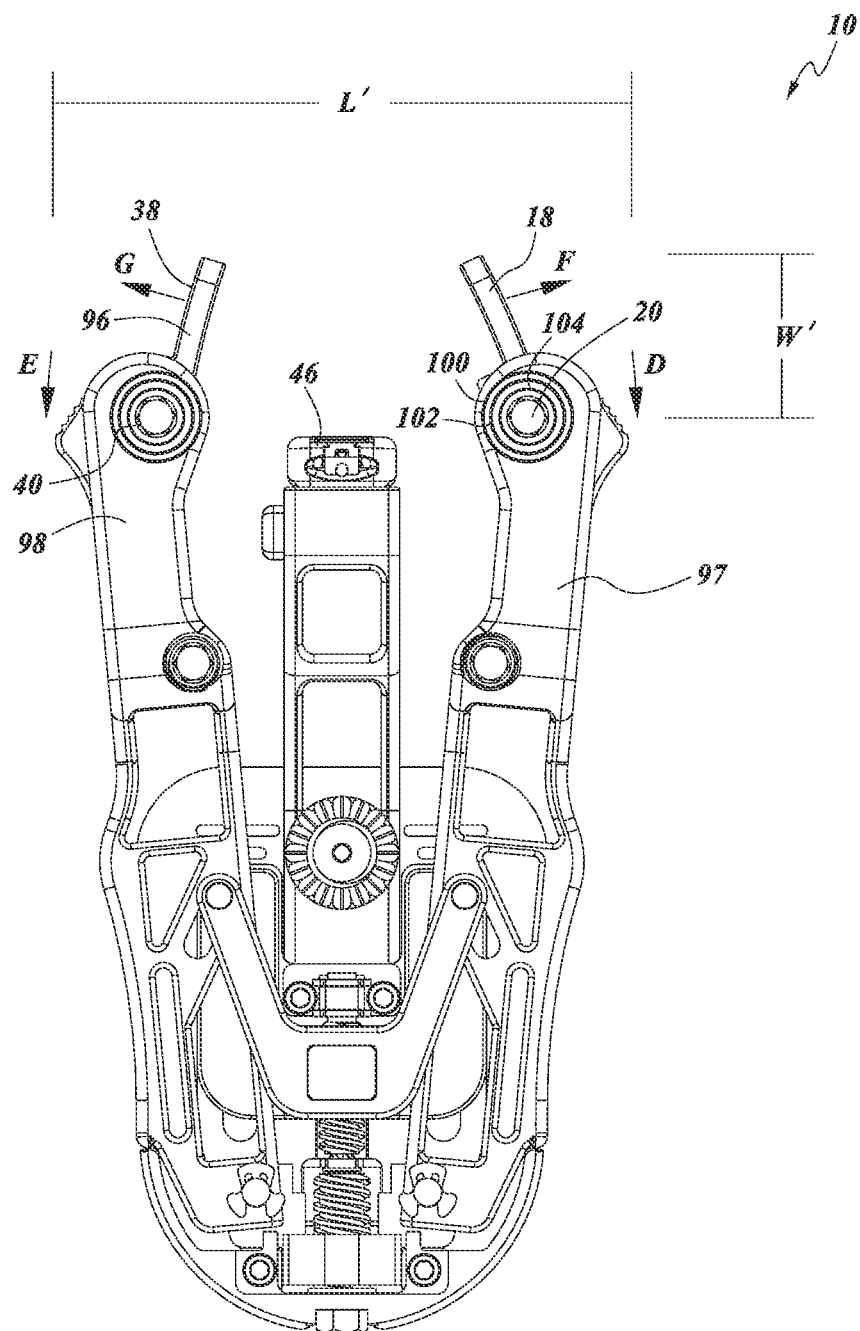
FIG. 7 provides a top view of the retractor of FIG. 6 in the rotated position.

In FIGS. 6-7, the retractor 10 is shown in the "rotated position," meaning that the first blade 18 is rotated relative to the third blade 46 and/or the second blade 38 is rotated relative to the third blade 46. While the application uses the phrase "the rotated position," it is understood that one or more positions may be described as rotated. For instance, the first blade 18 can be rotated at any angle relative to the third blade 46 greater than zero (e.g., 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, etc.), the second blade 38 can be rotated at any angle relative to the third blade 46 greater than zero (e.g., 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, etc.), the first blade 18 can be rotated approximately the same angle as the second blade 38, the first blade 18 can be rotated a different angle as the second blade 38, wherein the width W' in the rotated position is greater than the incision width or the width of any of the blades 18, 38, 46, or other rotated positions.

The width W' of the three blades 18, 38, 46 in this configuration is greater than the width W of any one blade, such as the width of the first blade 18 and the rail 64. The first blade 18 can rotate in a clockwise direction about the first axis 52. The second blade 38 can rotate in a counterclockwise direction about the second axis 54. The motion of the first blade 18 can be independent of the motion of the second blade 38. In other embodiments, the motion of the first blade 18 can be coupled to the motion of the second blade 38 such that rotation is controlled by a single rotation mechanism.

Figure 12:
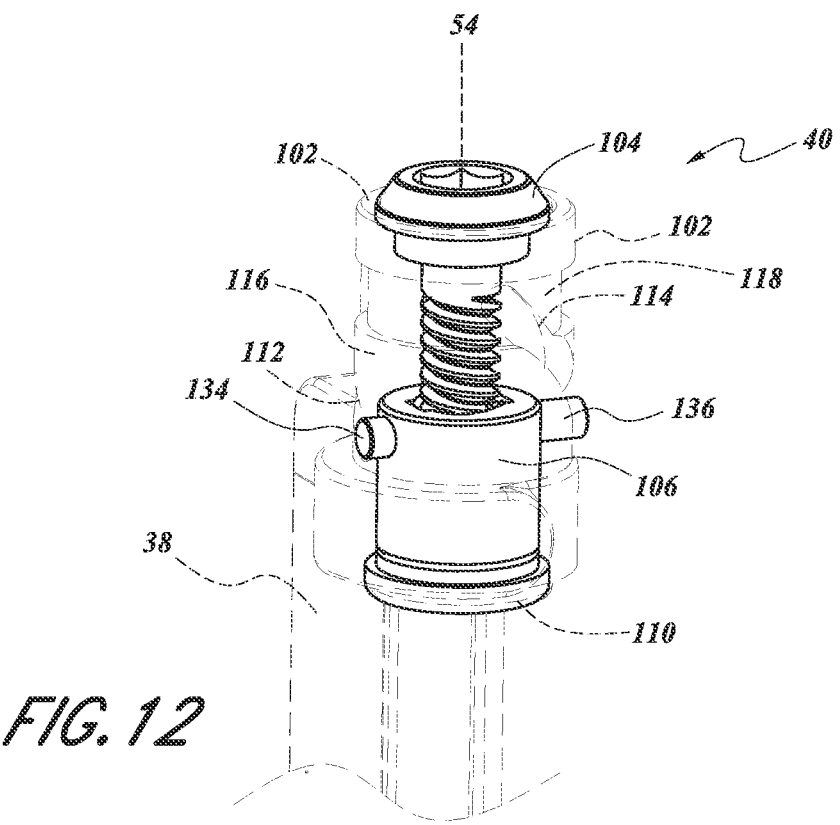
FIG. 12 provides a perspective view of a rotation mechanism of FIG. 1.
Figure 13:
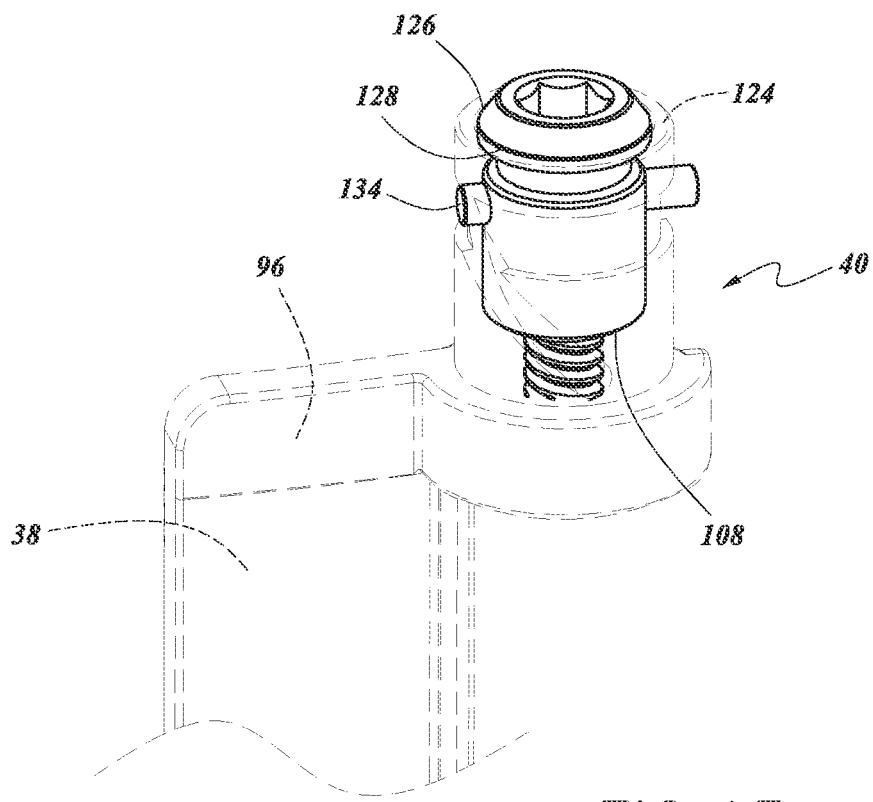
FIG. 13 provides a perspective view of a rotation mechanism of FIG. 11.
Figure 14:
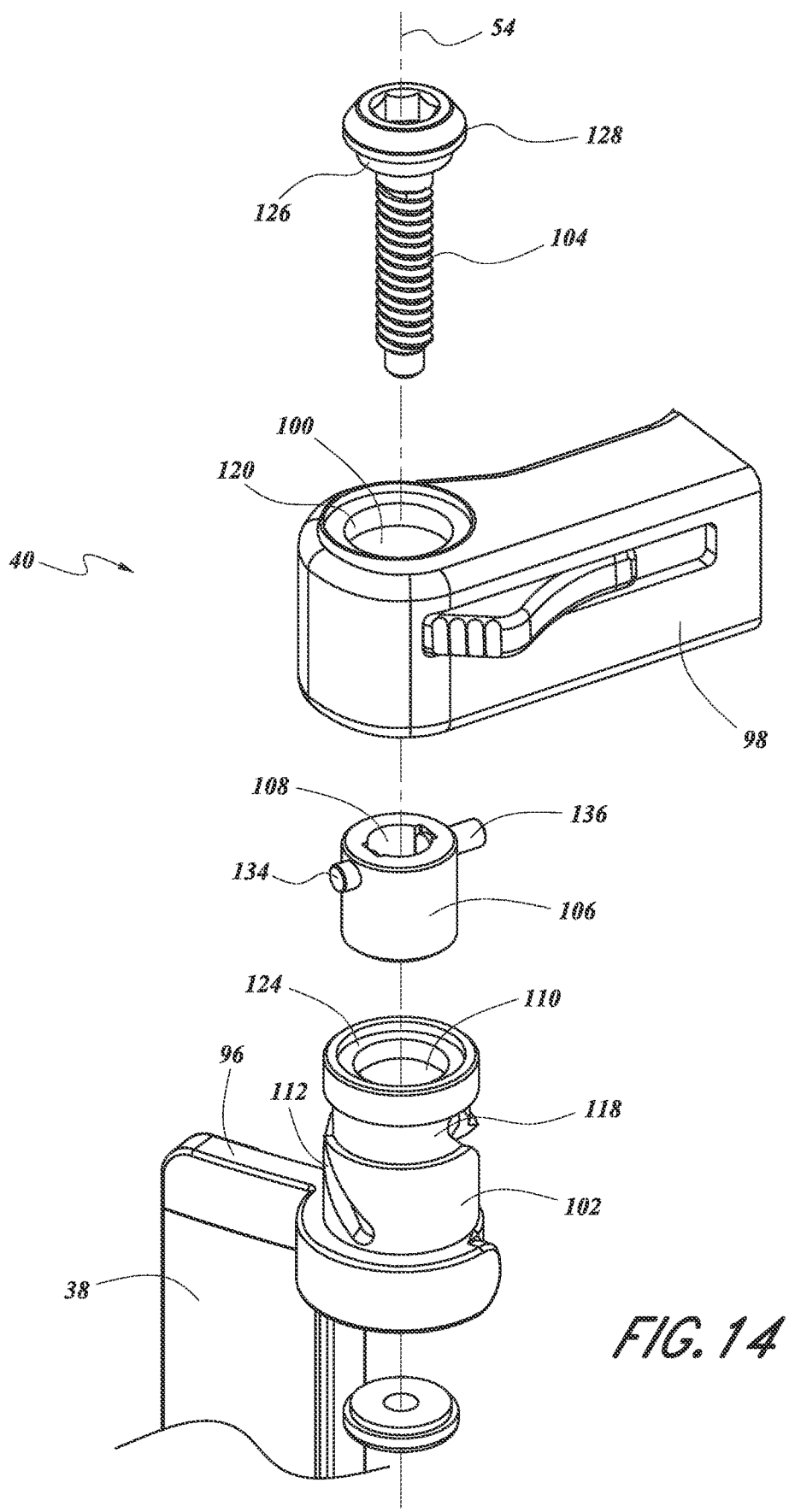
FIG. 14 provides an exploded view of a rotation mechanism of FIG. 1.

In the illustrated embodiment, the first blade 18 is rotated by a first rotation mechanism 20 and the second blade 38 is rotated by a second rotation mechanism 40. In some embodiments and methods of use, the first blade 18 can rotate in an opposite direction as the second blade 38 such that both blades open relative to the third blade 46. The first rotation mechanism 20 can be identical, substantially similar, or a mirror image of the second rotation mechanism 40. One embodiment of the first rotation mechanism 20 is shown in FIG. 12-14. Other embodiments are contemplated for rotating the first and/or second blades (e.g., various linkages, hinges and/or cams).

Referring to FIG. 7, turning the first rotation mechanism 20 about the first axis 52 in the direction of adjustment arrow D, results in rotation of the first blade 18. Turning the second rotation mechanism 40 about the second axis 54 in the direction of adjustment arrow E, results in rotation of the second blade 38, respectively. As shown in FIG. 7, rotating the first blade 18 causes the first blade 18 to exert force in the direction of direction arrow F, while rotating the second blade 38 causes the second blade 38 to exert force in the direction of direction arrow G. In some such embodiments, the first axis 52 and second axis 54 may be substantially coplanar with one another. Indeed in some embodiments, the first axis 52 and second axis 54 are not only coplanar but also substantially parallel to one another. In particular embodiments, the first axis 52 and second axis 54 are coplanar with, parallel to, or at some pre-determined skew angle with respect to one another.

In the illustrated embodiment, the first blade 18 is rotated and/or the second blade 38 is rotated after the first blade 18 is translated relative to the third blade 46 and the second blade 38 is translated relative to the third blade 46 along the third axis 56. Thus, after insertion in an incision of the blades 18, 38, 46 in the closed position, the retractor 10 is opened by the first blade 18 and the second blade 38 translating relative to the third blade 46 along the third axis 56 to achieve the opened position. Then the first blade 18 is rotated relative to the third blade 46 about the first axis 52 and/or the second blade 38 is rotated about the second axis 54 relative to the third blade 46 to achieve the rotated position. However, this depicts only some methods of use.

In some methods, the first blade 18 and/or the second blade 38 is rotated before the first blade 18 is translated relative to the third blade 46 and the second blade 38 is translated relative to the third blade 46 along the third axis 56. Thus, after insertion in an incision of the blades 18, 38, 46 in the closed position, the first blade 18 is rotated about the first axis 52 relative to the third blade 46 and/or the second blade 38 is rotated the second axis 54 relative to the third blade 46 to achieve the rotated position. Then the retractor 10 is opened by the first blade 18 and the second blade 38 translating relative to the third blade 46 along the third axis 56 to achieve the opened position. Then, if needed, the first blade 18 and/or the second blade 38 is rotated again relative to the third blade 46 to achieve the rotated position (e.g., another rotated position within the broad definition of the "rotated position").

The rotated position creates and maintains an aperture in the incised tissue that is wider W' (i.e. dimensionally larger in a direction perpendicular or oblique to the direction of the incision) than the incision. If the first blade 18 and/or second blade 38 are rotated after the blades 16, 38 have been translated relative to the third blade, then the retractor 10 creates and maintains an aperture in the incised tissue that is both longer L' due to the translation (i.e. dimensionally larger in the direction of the incision) and wider W' due to the rotation (i.e. dimensionally larger in a direction perpendicular or oblique to the direction of the incision) than the incision.

It is to be understood that, while this description is especially apt where the incision is a straight line incision of about 0.1 to about 3 inches in length, it can apply to any shape of incision (e.g. an arc, a sinusoid, etc.) of any length. In particular embodiments, the contemplated size of the incision is about 0.5 to 2 inches in length and the blades 18, 38, 46 are appropriately sized so that when the retractor 10 is in the closed position the blades 18, 38, 46 fit lengthwise within the incision without requiring substantial stretching of the incised tissue prior to opening of the retractor 10. Thus, in some embodiments, the blades 18, 38, 46 are sized to snugly fit within the incision when the retractor 10 is in the closed position.

Figure 8:
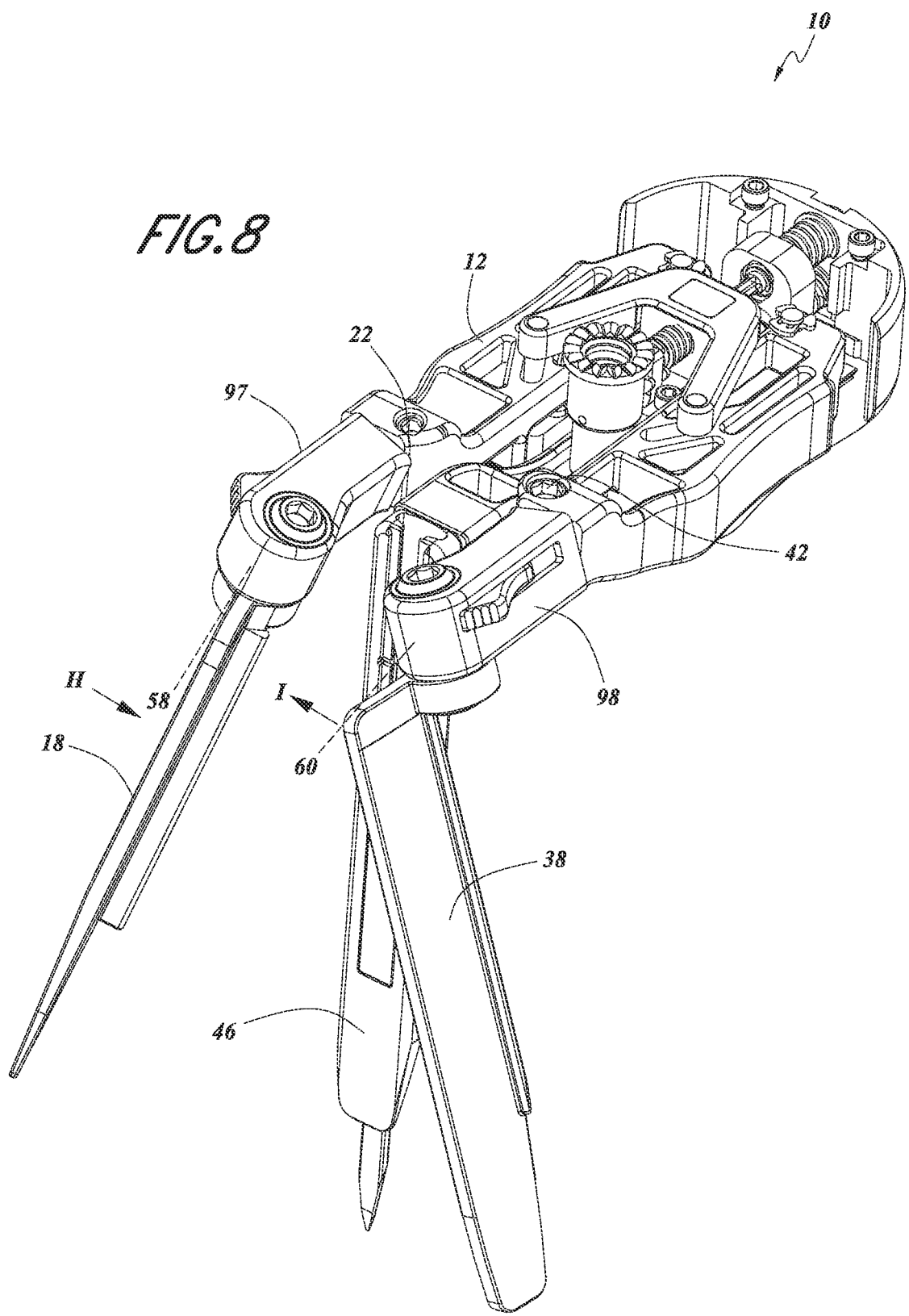
FIG. 8 provides a perspective view of the retractor of FIG. 6 in the pivoted position. Opening the retractor along these axes stretches the incision along its width and/or length.
Figure 9:
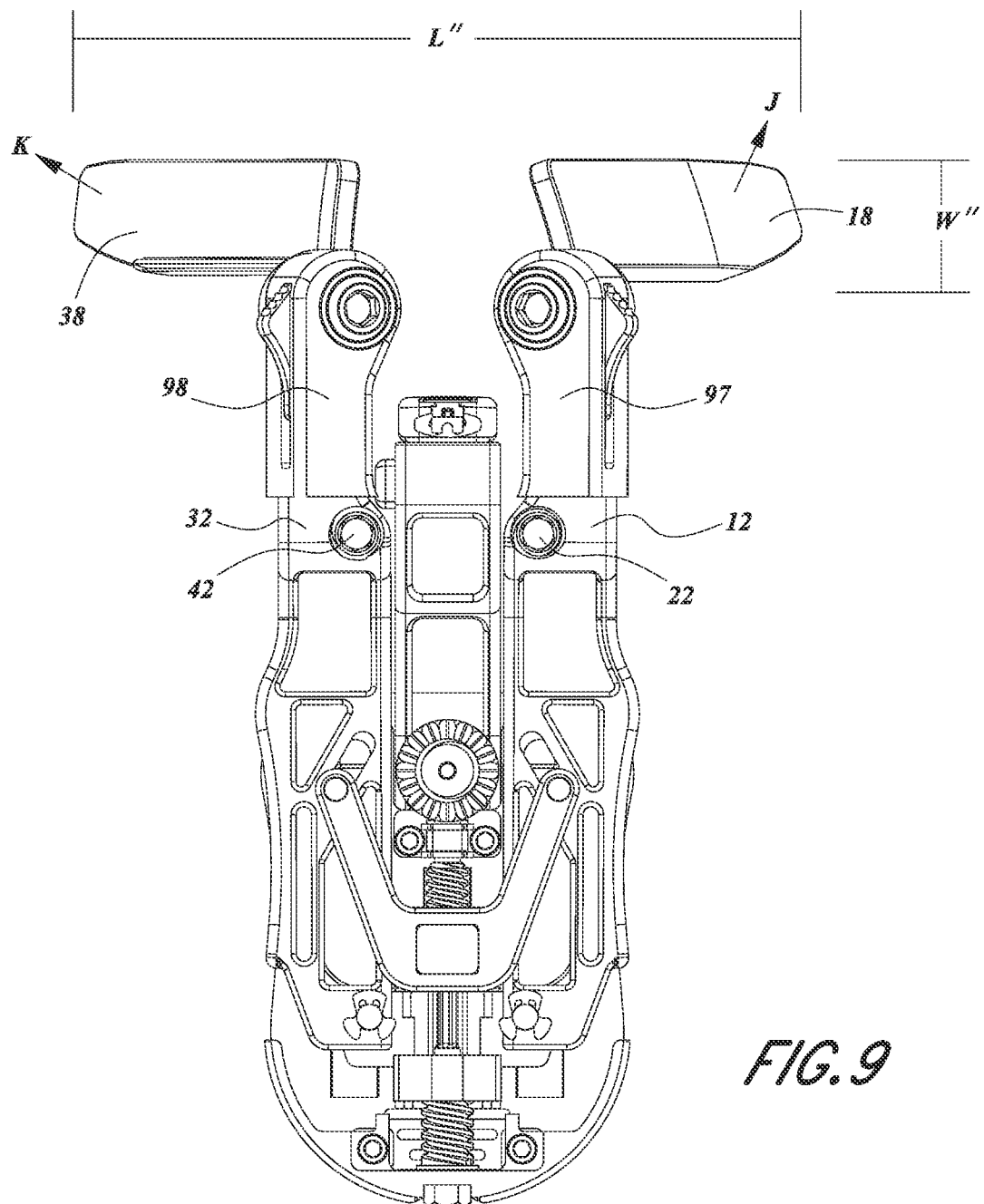
FIG. 9 provides a top view of the retractor of FIG. 8 in the pivoted position.

In FIGS. 8-9, the retractor 10 is shown in the "pivoted position," meaning that the first blade 18 is pivoted relative to the third blade 46 and/or the second blade 38 is pivoted relative to the third blade 46. While the application uses the phrase "the pivoted position," it is understood that one or more positions may be described as pivoted. For instance, the first blade 18 can be pivoted at any angle relative to the third blade 46 greater than zero (e.g., 5°, 10°, 15°, 20°, 25°, 30°, 35°, 40°, 45°, 50°, 55°, 60°, 65°, 70°, 75°, 80°, 85°, 90°, 95° 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, etc.), the second blade 38 can be pivoted at any angle relative to the third blade 46 greater than zero (e.g., 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, etc.), the first blade 18 can be pivoted approximately the same angle as the second blade 38, the first blade 18 can be pivoted a different angle as the second blade 38, wherein the length L" and/or the width W" in the pivoted position is greater than the incision length or width or the length or width of any of the blades 18, 38, 46, or other pivoted positions.

The width W" of the three blades 18, 38, 46 in this configuration is greater than the width W of any one blade, such as the width of the first blade 18 and the rail 64. The length L" of the three blades 18, 38, 46 in this configuration is greater than the length L of any one blade, such as the length of the first blade 18. The first blade 18 can pivot in a clockwise direction about the fourth axis 58. The second blade 38 can pivot in a counterclockwise direction about the fifth axis 60. The motion of the first blade 18 can be independent of the motion of the second blade 38. In other embodiments, the motion of the first blade 18 can be coupled to the motion of the second blade 38 such that pivoting is controlled by a single pivot mechanism. The pivoted position creates and maintains an aperture in the incised tissue that is both longer L" (i.e. dimensionally larger in the direction of the incision) and wider W" (i.e. dimensionally larger in a direction perpendicular or oblique to the direction of the incision) than the incision.

In the illustrated embodiment, the fourth axis 58 is perpendicular to the first axis 52. The first blade 18 can rotate about the first axis 52 and pivot about the fourth axis 58. This provides at least two degrees of freedom for the first blade 18 and allows the first blade 18 to be positioned in a variety of locations within the incision. In the illustrated embodiment, the fifth axis 60 is perpendicular to the second axis 54. The second blade 38 can rotate about the second axis 54 and pivot about the fifth axis 60. This provides at least two degrees of freedom for the second blade 38 and allows the second blade 38 to be positioned in a variety of locations within the incision. The fourth axis 58 and the fifth axis 60 are perpendicular to the third axis 56. The movement along the third axis 56 provides an extra degree of freedom.

In the illustrated embodiment, the first blade 18 is pivoted by a first pivot mechanism 22 and the second blade 38 is pivoted by a second pivot mechanism 42. The first blade 18 can pivot in an opposite direction as the second blade 38 such that both blades 18, 38, open relative to the third blade 46. The first pivot mechanism 22 can be identical, substantially similar, or a mirror image of the second pivot mechanism 42. One embodiment of the first pivot mechanism 22 is shown in in FIGS. 15-16. Other embodiments are contemplated for providing the described pivoting motions such as, for example, various linkages, cams and/or hinges.

Referring to FIG. 9, pivoting the first pivot mechanism 22 about the fourth axis 58 in the direction of adjustment arrow H, results in rotation of the first blade 18. Turning the second pivot mechanism 42 about the fifth axis 60 in the direction of adjustment arrow I, results in rotation of the second blade 38, respectively. Pivoting the first blade 18 causes the first blade 18 to exert force in the direction of direction arrow J, while pivoting the second blade 38 causes the second blade 38 to exert force in the direction of direction arrow K.

In some examples, the first axis 52 is substantially perpendicular or perpendicular to the fourth axis 58. In particular embodiments, the first axis 52 is at some pre-determined skew angle with respect to the fourth axis 58. In some examples, the second axis 54 is substantially perpendicular or perpendicular to the fifth axis 60. In particular embodiments, the second axis 54 is at some pre-determined skew angle with respect the fifth axis 60. In some examples, the third axis 56 is substantially perpendicular or perpendicular to the fourth axis 58, the fifth axis 60 or both the fourth axis 58 and the fifth axis 60. In some embodiments, the third axis 56 is substantially perpendicular or perpendicular to both the fourth axis 58 and the fifth axis 60. In some embodiments, the third axis 56 is perpendicular or substantially perpendicular to the fourth axis 58, the fifth axis 60 or both the fourth axis 58 and the fifth axis 60. In some embodiments, the third axis 56 is perpendicular or substantially perpendicular to both the fourth axis 58 and the fifth axis 60.

In some embodiments, the third blade 46 can be pivoted about a seventh axis (not shown) that is parallel to the third axis 56 and extends from near the connection between the third blade 46 and the body 26. In some embodiments, the third arm 50 can have a hinge that pivots the third blade 46. The third blade 46 can be pivoted at any angle relative to the vertical plane greater than zero (e.g., 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, etc.). The third blade 46 can be pivoted a same angle or a different angle as the first blade 18 and/or second blade 38, wherein the length L" and/or the width W" in the pivoted position is greater than the incision length or width or the length or width of any of the blades 18, 38, 46, or other pivoted positions. The seventh axis is described in some embodiments as substantially parallel or parallel to the third axis 56. In other embodiments, the seventh axis can be at some pre-determined skew angle with respect to the third axis 56.

The width W" of the three blades 18, 38, 46 in this configuration is greater than the width W of any one blade, such as the width of the third blade 46. The length L" of the three blades 18, 38, 46 in this configuration is greater than the length L of any one blade, such as the length of the third blade 46. The first blade 18 can pivot in a clockwise direction about the fourth axis 58. The second blade 38 can pivot in a counterclockwise direction about the fifth axis 60. The third blade 46 can pivot about the seventh axis toward the proximal direction. The motion of the third blade 46 can be independent of the motion of the first blade 18 and the second blade 38. In other embodiments, the motion of the third blade 46 can be coupled to the motion of the first blade 18 and/or the second blade 38 such that pivoting is controlled by a single pivot mechanism. The pivoted position creates and maintains an aperture in the incised tissue that is both longer L" (i.e. dimensionally larger in the direction of the incision) and wider W" (i.e. dimensionally larger in a direction perpendicular or oblique to the direction of the incision) than the incision.

The third blade 46 can be pivoted by a pivot mechanism that is identical or substantially similar to the pivot mechanism described herein for the first blade 18 and second blade 38. Other embodiments are contemplated for providing the described pivoting motions such as, for example, various linkages, cams, hinges, gears and/or levers.

In the illustrated embodiment, the first blade 18 is pivoted and/or the second blade 38 is pivoted after the first blade 18 is rotated and/or the second blade 38 is rotated and after the first blade 18 is translated relative to the third blade 46 and the second blade 38 is translated relative to the third blade 46. Thus, after insertion in an incision of the blades 18, 38, 46 in the closed position, the retractor 10 is opened by the first blade 18 and the second blade 38 translating along the third axis 56 relative to the third blade 46 to achieve the opened position. Then the first blade 18 is rotated about the first axis 52 relative to the third blade 46 and/or the second blade 38 is rotated about the second axis 54 relative to the third blade 46 to achieve the rotated position. Then the first blade 18 is pivoted about the fourth axis 58 relative to the third blade 46 and/or the second blade 38 is pivoted about the fifth axis 60 relative to the third blade 46 to achieve the pivoted position. In some embodiments, the third blade 46 is pivoted about the third axis 56 toward the proximal direction. However, this depicts only some methods of use.

In some methods, the first blade 18 is pivoted and/or the second blade 38 is pivoted and/or the third blade 46 is pivoted before the first blade 18 and/or the second blade 38 is rotated. In some methods, the first blade 18 is pivoted and/or the second blade 38 and/or the third blade 46 is pivoted is pivoted before the first blade 18 is translated relative to the third blade 46 and the second blade 38 is translated relative to the third blade 46.

Figure 11:
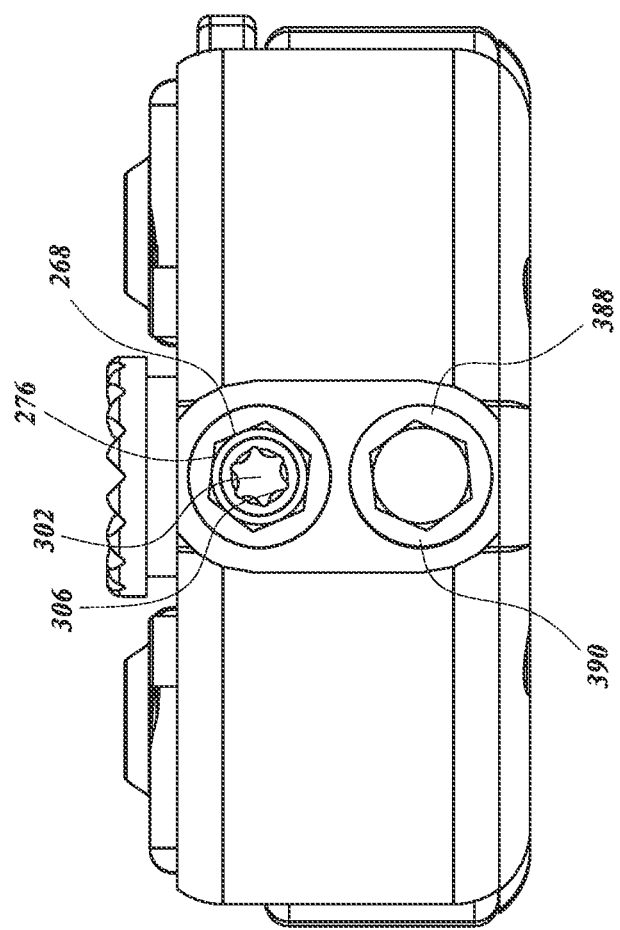
FIG. 11 provides a proximal view of the retractor of FIG. 10.
Figure 15:
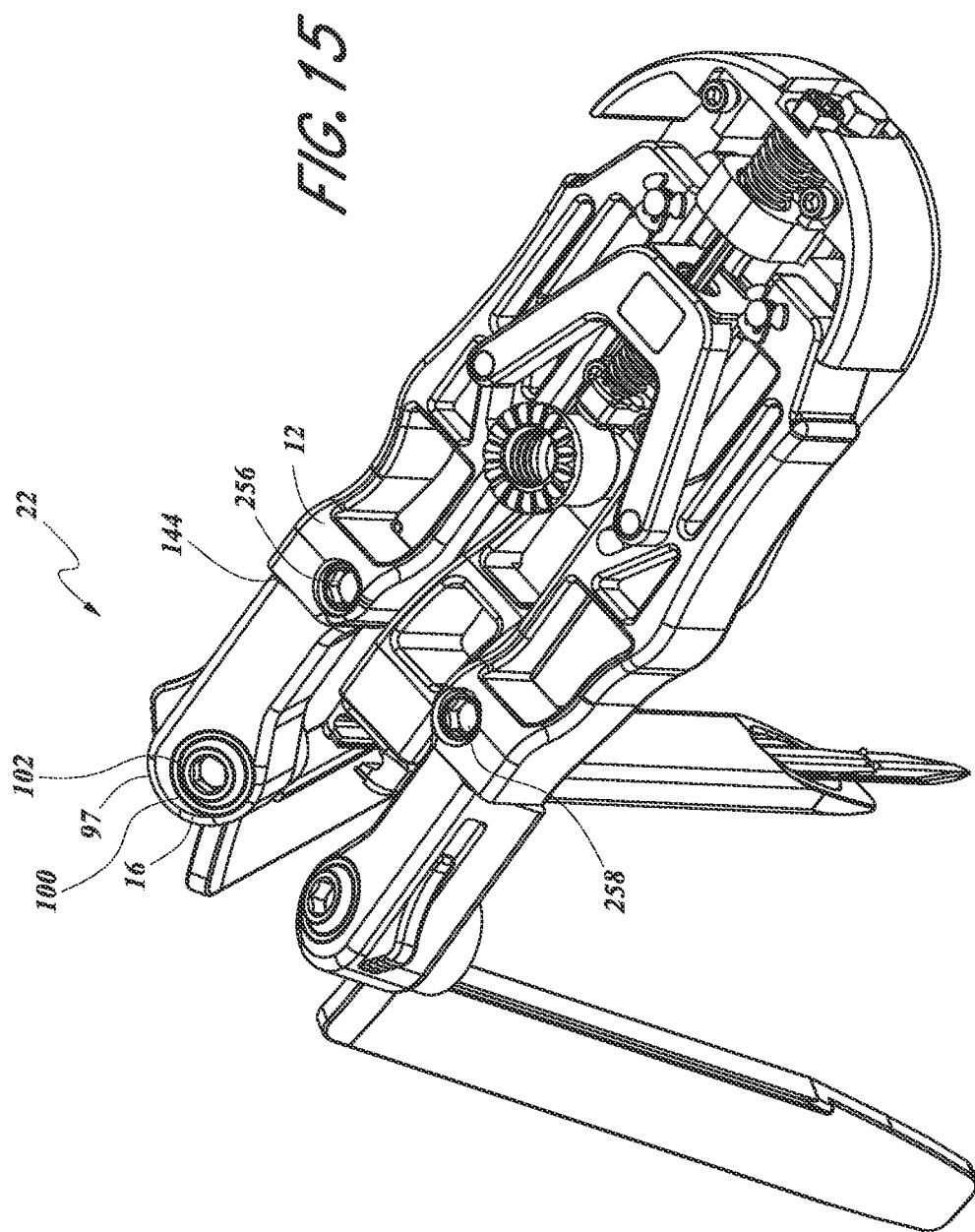
FIG. 15 provides a perspective view a pivot mechanism of FIG. 1.
Figure 16:
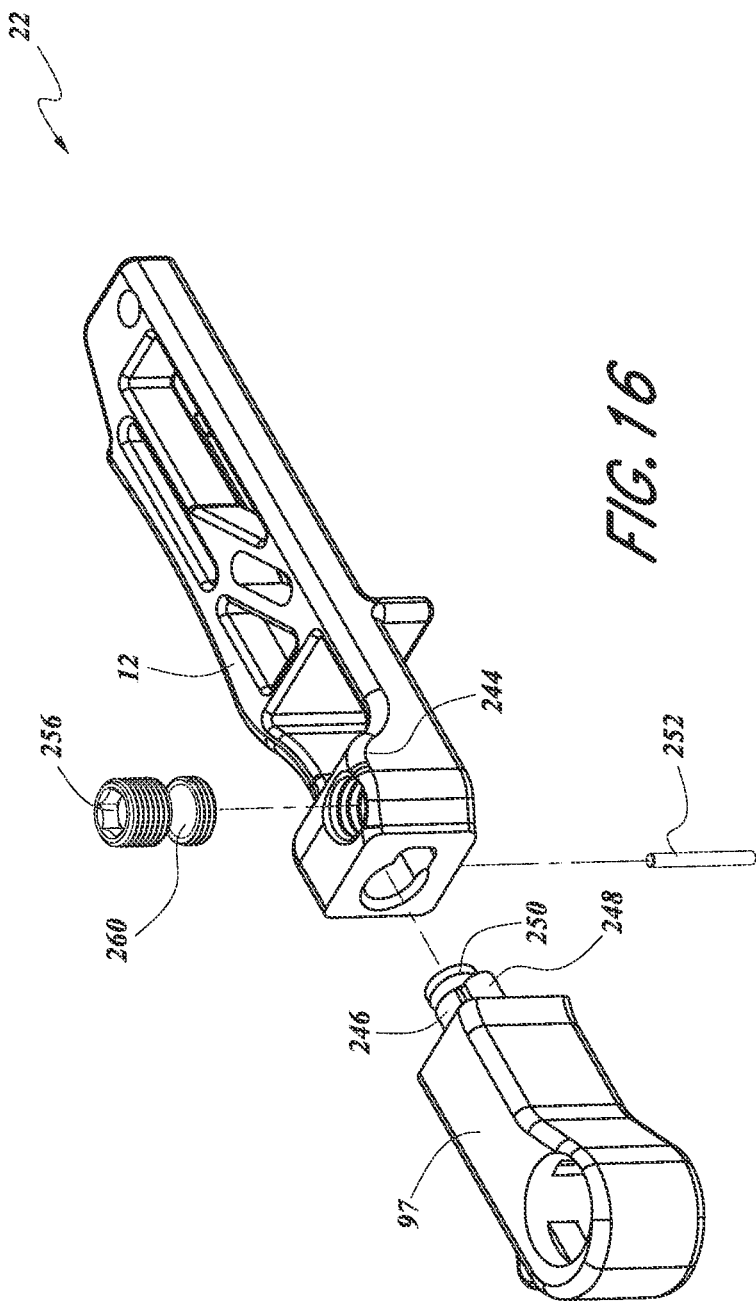
FIG. 16 provides an exploded view of a pivot mechanism of FIG. 14.

FIGS. 10-16 show embodiments of the various mechanisms of the retractor 10. FIG. 10 shows the spread mechanism 34. The spread mechanism 34 is a device for translating the first blade 18 and the second blade 38 about the third axis 56. FIG. 11 shows the proximal end of the retractor 10 which includes the actuator for the spread mechanism 34. FIGS. 12-14 show the rotation mechanism 40. The rotation mechanism 40 is a device for rotating the second blade 38 about the second axis 54. The rotation mechanism 40 can be identical, substantially similar or a mirror image of the rotation mechanism 20 shown in FIG. 1. The rotation mechanism 20 is a device for rotating the first blade 18 about the first axis 52. FIGS. 15-16 show the pivot mechanism 22. The pivot mechanism 22 is a device for pivoting the first blade 18 about the fourth axis 58. The pivot mechanism 42 can be identical, substantially similar or a mirror image of the pivot mechanism 22. The pivot mechanism 42 is a device for pivoting the second blade 38 about the fifth axis 60. Other configurations are possible for rotating the blades as described herein e.g., various levers, knobs, cams, etc.

FIG. 10 shows the spread mechanism 34. The retractor 10 can include the carriage 264. The carriage 264 can have a v-shaped configuration. The carriage 264 can have a first carriage arm 288 and a second carriage arm 290. Each carriage arm 288, 290 can form an angle alpha, beta with a longitudinal axis 292 of the body 26. The angle alpha can be the same as the angle beta, or the angles alpha, beta can be different. Each carriage arm 288, 290 can include a pin 294, 296. The pin 294 of the first carriage arm 288 can be connected to a slot 298 in the first arm 12. The pin 296 of the second carriage arm 290 can be connected to a slot 300 in the second arm 32. The pins 294, 296 can be received within the slots 298, 300 allowing the arms 12, 32 to move about the pins 294, 296 and allow the blade assemblies 16, 36 to translate along the third axis 56.

The retractor 10 can be in the "opened position," meaning that the first arm 12 and the second arm 32 are displaced relative to the third blade 46 along the third axis 56. While the application uses the phrase "opened position," it is understood that one or more positions may be described as open. The carriage 264 can be mounted onto a screw 304. The screw 304 can be located along the sixth axis 62. The screw 304 can extend in the proximal-distal direction of the body 26. The screw 304 can include external threads that engage complementary internal threads on the carriage 264. The screw 304 can be configured to mate with a bearing (not shown) in the carriage 264. The bearing allows the screw 304 to rotate without translation (e.g., rotate in place). In some configurations, the carriage 264 translates along the screw 304 as the screw 304 rotates.

The retractor 10 can include an actuator 302. The actuator 302 interacts with the arms 12, 32 to spread the arms 12, 32. In the illustrated embodiment, the actuator 302 rotates the screw 304 in the direction of arrow A. In some embodiments, the actuator 302 can include an inner engagement 306 that abuts a proximal end of the body 26. The inner engagement 306 can include a plurality of flats designed to engage a driver. Other configurations are contemplated. In some embodiments, the actuator 302 is located within another actuator as shown in FIG. 11.

Rotation of the actuator 302 causes the carriage 264 to translate from the proximal end of the body 26 toward the distal end of the body 26. The carriage 264 is coupled to the pins 294, 296. As the carriage 264 translates forward, the pins 294, 296 also translate forward. The slots 298, 300 can be elongate channels that extend at an angle to the forward-aft direction of the movement of the pins 294, 296. The pins 294, 296 can exert a force on the slots 298, 300 of the arms 12, 32 as the pins 294, 296 move forward or aft. The angle of the slots 298, 300 causes the arms 12, 32 to spread. The arms 12, 32 can pivot about their connection points to the carriage 264. The shape of the slots 298, 300 can cause the arms 12, 32 to spread outward along the third axis 56. One skilled in the art will recognize that the carriage 264 can spread the arms 12, 32 in either direction.

The actuator 302 can translate the blades 18, 38 along the third axis 56 irrespective of the location of the carriage 264 relative to the body 26, as described herein with respect to the slide mechanism 28. The rotation mechanisms 20, 40 can rotate the blades 18, 38 irrespective of the location of the carriage 264 relative to the body 26. The pivot mechanisms 22, 42 can pivot the blades 18, 38 irrespective of the location of the carriage 264 relative to the body 26.

FIGS. 12-13 are perspective views of the second blade 38 in the closed position and the rotated position, respectively. FIG. 14 is an exploded view of the rotation mechanism 40. Referring back to FIGS. 1, 6-7, these figures depict an embodiment of a second blade assembly 36, which comprises the second blade 38. The second blade assembly 36 comprises a hub 98. The hub 98 is coupled to the distal end of the second arm 32. In the illustrated embodiment, the hub 98 houses the rotation mechanism 40. Also shown in these views is the second axis 54 to achieve the rotated position. In some embodiments, the second blade 38 is adapted to rotate about the second axis 54. In some embodiments, this added degree of freedom permit the second blade 38 to be rotated outward so that the second blade 38 is farther apart from the third blade 46. The third blade 46, in some embodiments, remains stationary. FIG. 6 shows a perspective view of the retractor 10 with the first blade 18 and the second blade 38 in a rotated position. FIG. 7 shows a top view of FIG. 6.

The hub 98 can have a first connecting hole 100. The first connecting hole 100 can be non-threaded. The hub 98 is coupled to an inner barrel 102. In the illustrated embodiment the inner barrel 102 is integrally formed with the second blade 38. In other embodiments, the inner barrel 102 can be coupled with the second blade 38. The second blade 38 can be connected to the second bridge 96 which can be connected to the inner barrel 102. The inner barrel 102 can be sized to be accepted within the first connecting hole 100 of the hub 98.

Referring to FIGS. 12-14, the second rotation mechanism 40 can include a screw 104. The second rotation mechanism 40 can include a collar 106. The collar 106 can include a threaded bore 108 sized to receive the screw 104. The screw 104 and the collar 106 are sized to be received in a lumen 110 of the inner barrel 102. The inner barrel 102 can have a first slot 112 and a second slot 114 cut into the upper portion 116 of the inner barrel 102. The first slot 112 can be offset 180 degrees from the second slot 114. Specifically, the upper portion 116 of the inner barrel 102 is that portion of the inner barrel 102 above the highest point at which the second bridge 96 connects to the inner barrel 102. The first slot 112 and second slot 114 can extend from near the top of the inner barrel 102 to the bottom of the inner barrel 102. The slots 112, 114 extend diagonally across the upper portion 116. Although two slots 112, 114 are shown, other configurations are contemplated (e.g., one slot, three slots, four slots, five slots). The one or more slots may have the same slope and extend in the same direction.

The inner barrel 102 can have an engagement groove 118 circumscribing the inner barrel 102 above the slots 112, 114. An appropriately sized retention member can be received within the groove 118. The retention member allows the inner barrel 102 to rotate but not translate within the first connecting hole 100.

The lumen 110 can have an engagement groove 124 circumscribing the lumen 110 above the slots 112, 114. The screw 104 can have a complementary engagement groove 126 circumscribing the head of the screw 104. An appropriately sized retention member 128 such as an o-ring can be received within the grooves 124, 126. The retention member 128 allows the screw 104 to rotate but not translate within the inner barrel 102.

FIGS. 12-14 further depict a first connector pin 134 and second connector pin 136. The number of pins equals the number of slots. The connector pins 134, 136 extend outward from the collar 106. In the illustrated embodiment, the first connector pin 134 is offset 180 degrees from the second connector pin 136. Other configurations are contemplated. The first connector pin 134 is sized to extend through the first slot 112 and the second connector pin 136 is sized to extend through the second slot 114.

The screw 104 fits within the threaded bore 108 of the collar 106, as depicted in FIGS. 12-13. In this configuration, the first slot 112 forms a passage through which the first connector pin 134 fits. The second slot 114 forms a passage through which the second connector pin 136 fits. As depicted in FIG. 12, the second blade 38 can be in the closed position when the first connector pin 134 is at the bottom of the first slot 112 and the second connector pin 136 is at the bottom of the second slot 114. In this configuration, as shown in FIG. 4 it is seen that the second blade 38, and the third blade 46 stack to form a substantially planar blade set.

One skilled in the art will recognize that rotating the screw 104 can cause the collar 106 to translate up and down. The retention member 128 prevents the screw 104 from translating. The connector pins 134, 136 can be rigidly coupled to the collar 106. At least one connector pin 134 or 136 can be retained in the channel 122 of the hub 98, which prevents the collar 106 from rotating. Rotating the screw 104 will force the collar 106 to rise since the screw 104 cannot translate and the collar 106 cannot rotate. The connector pins 134, 136 will similarly rise with the collar 106. As the connector pins 134, 136 rise, they act upon the slots 112, 114. Due to the shape of the slots 112, 114, the inner barrel 102 will rotate as the connector pins 134, 136 rise. Rotation of the inner barrel 102 also rotates the second blade 38. In other words, rotating the screw 104 forces the connector pins 134, 136 to rise and act upon the slots 112, 114, thereby causing the inner barrel 102 to rotate, and also rotate the second blade 38 about the second axis 54. One skilled in the art will understand that the first blade 18 can be rotated in the other direction (e.g., counterclockwise to close the first blade 18). Starting with the connector pins 134, 136 at the top of slots 112, 114, translating the collar 106 downward will force the connector pins 134, 136 to move down the length of the screw 104 in the slots 112, 114, thereby causing the inner barrel 102 to rotate, thereby causing the second blade 38 to rotate about the second axis 54.

As can be seen in FIG. 14, the assembly of inner barrel 102, the collar 106, the screw 104, and the connector pins 134, 136, fits through the first connecting hole 100 of the hub 98. As can be seen in FIGS. 6-7, the head of the screw 104 is visible through the hub 98 allowing the screw 104 to be manipulated. One of skill in the art will appreciate that the connector pins 134, 136 engage the slots 112, 114, thereby permitting the inner barrel 102 to freely turn about the second axis 54. The retention member (not shown) prevents the inner barrel 102 from moving up or down along the second axis 54. The retention member 128 can prevent the screw 104 from moving up or down along the second axis 54. Turning the screw 104 about the second axis 54 in one direction can cause the collar 106 to move upward along the second axis 54, while turning the screw 104 in the opposite direction can cause the collar 106 to move downward along the second axis 54. As explained above, movement of the collar 106 forces movement of the connector pins 134, 136 up and down the second axis 54. Movement of the connector pins 134, 136 in one direction can create force in one direction on the slots 112, 114 in the inner barrel 102 causing the inner barrel 102 to rotate. The screw 104 can be turned to rotate the second blade 38 toward or away from the third blade 46. In the illustrated embodiment, the second blade 38 is connected to a second bridge 96, which in turn is connected to the inner barrel 102 such that rotating the inner barrel 102 about second axis 54 clockwise can result in the second blade 38 also turning to clockwise.

The first blade assembly 16 can be substantially similar to the embodiment of the second blade assembly 36 described herein. For instance, the first blade assembly 16 can include an inner barrel similar to inner barrel 102, screw similar to screw 104, collar similar to collar 106, and connecting pins similar to connecting pins 134, 136. In some embodiments, the first blade assembly 16 rotates clockwise about the first axis 52 away from the third blade 46 and the second blade assembly 36 rotates counterclockwise about the second axis 54 away from the third blade 46. In this configuration, the inner barrel of the second blade assembly 36 can be a mirror image of the first blade assembly 16. For instance, the first blade assembly 16 can have one slot which is the mirror image of first slot 112 and another slot which is the mirror image of second slot 114. This slot configuration allows the first blade 18 to rotate clockwise, the opposite direction as the second blade 38 described herein. The function of the connector pins of the first blade assembly 16 and the method of rotation can be substantially similar.

FIG. 15 is a perspective view of the first blade assembly 16 in the pivoted position. FIG. 16 is an exploded view of the pivot mechanism 22. Referring back to FIGS. 8-9, these figures depict an embodiment of a first blade assembly 16, which comprises the first blade 18. The first blade assembly 16 comprises the hub 97. The hub 97 can be similar, identical or a mirror image of the hub 98 described with respect to FIGS. 12-14. The hubs 97, 98 can interact with the arms 12, 32 to pivot the hubs 97, 98. The hub 97 is coupled to the first arm 12. In the illustrated embodiment, the hub 97 and the first arm 12 house the pivot mechanism 22. The arm 12 can have a second connecting hole 242 and a third connecting hole 244.

The hub 97 can include a post 246. The post 246 can be integrally formed with the hub 97. In some embodiments, the post 246 is a separate component from the hub 97 and the post 246 can be rigidly coupled to the hub 97 such that movement of the post 246 causes movement of the hub 97. The post 246 can be accepted into a bore (not shown) of the first arm 12. The post 246 can have a round cross-section but other shapes are contemplated. The post 246 can have a boss 248 extending along a portion of the length of the post 246. The boss 248 can have a substantially semi-circular cross-section but other shapes are contemplated. The boss 248 can be rounded. The boss 248 can be integrally formed with the post 246. The boss 248 can be rigidly coupled to the post 246 such that movement of the boss 248 causes movement of the post 246.

The post 246 can have a groove 250 circumscribing post 246. The groove 250 can be toward the proximal end of the post 246 that extends into the bore. The first arm 12 can include the second connecting hole 242. The second connecting hole 242 can be sized to accept a pin 252. The upper portion of the pin 252 can fit within the second connecting hole 242. The lower portion of the pin 242 can fit within the groove 250 of the post 246. The pin 242 facilitates alignment between the boss 248 and the screw 256, described herein. The second connecting hole 242 can be non-threaded.

The first blade 18 can be pivoted by rotating a screw 256. The second blade 38 can be pivoted by rotating a screw 258. The screws 256, 258 can be a hex screw. As shown in FIG. 16, the first arm 12 can include the third connecting hole 244. The third connecting hole 244 can be threaded. The screw 256 can be accepted into the third connecting hole 244. The screw 256 can include a cutout 260. The cutout 260 can have a complementary shape to the boss 248 extending from the post 246. The boss 248 can be captured by the cutout 260 in the screw 256. The boss 248 of the post 246 and the cutout 260 of the screw 256 can pivot the hub 97 relative to the first arm 12.

One skilled in the art will recognize that rotating the screw 256 can cause the screw 256 to translate within the third connecting hole 244. The translation of the screw 256 can exert a force on the boss 248 causing the boss 248 to rotate. The translation of the screw 256 can exert a force on the post 246 causing the post 246 to rotate. The force acting on the boss 248 and the post 246 can cause the hub 97 to pivot. As the hub 97 pivots, the pin 252 will follow the groove 250 of the post 246. The pin 252 and the groove 250 maintain contact between the boss 248 and the screw 256 as the screw 256 is rotated. As the screw 256 is moved up and down, the boss 248 is moved up and down to rotate the hub 97, which pivots the first blade 18. The design benefits from direct drive of the post 246 (i.e., the screw 256 positively engages and rotates the post 246 in both directions) and may avoid fatigue of the pivot mechanism 22, which can occur in other designs having springs, torsion bars, or other non-direct drive configurations in one or more directions. Fatigue can cause unintentional blade tilting.

Pivoting of the hub 97 can result in the pivoting of the inner barrel 102 received in the first connecting hole 100. Pivoting the inner barrel 102 can also pivot the first blade 18. In other words, rotating the screw 256 will cause the hub 97 to pivot, thereby pivoting the inner barrel 102 coupled to the first blade 18 and the first blade 18. One skilled in the art will recognize that the first blade 18 can be pivoted in either direction based on the rotation of the screw 256. The longitudinal axis of the post 246 can corresponds to the fourth axis 58. The longitudinal axis of the post 246 can be offset from a longitudinal axis of the hub 97.

The second blade assembly 36 can be similar to the embodiments described herein. For instance, the second blade assembly 36 can include a post similar to post 246, a pin similar to pin 252, and a screw 258 similar to screw 256. In some embodiments, the first blade assembly 16 rotates counterclockwise about the post 246 and the second blade assembly 36 rotates clockwise about a similar post when viewed from the proximal end of the retractor 10. In some configurations, the second blade assembly 36 can be a mirror image of the first blade assembly 16. For instance, the screw 258 of the second assembly 36 can be threaded in the opposite direction as the screw 256 of the first assembly 16. This configuration of the screws 256, 258 allow the second blade 38 to pivot in the opposite direction as the first blade 18 described herein. The function of the screws, pins and the posts of the second blade assembly 36 and the method of rotation of the screw can be similar.

Figure 17:
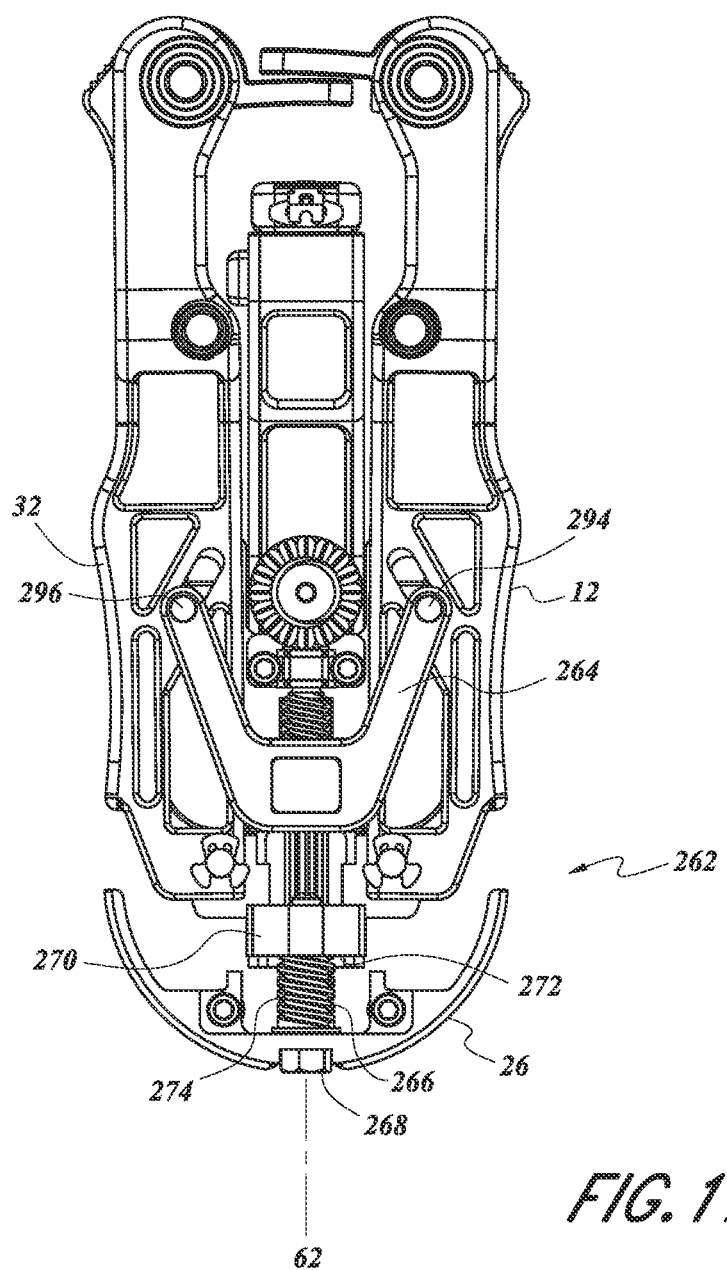
FIG. 17 provides a perspective view of a slide mechanism of FIG. 1.
Figure 18:
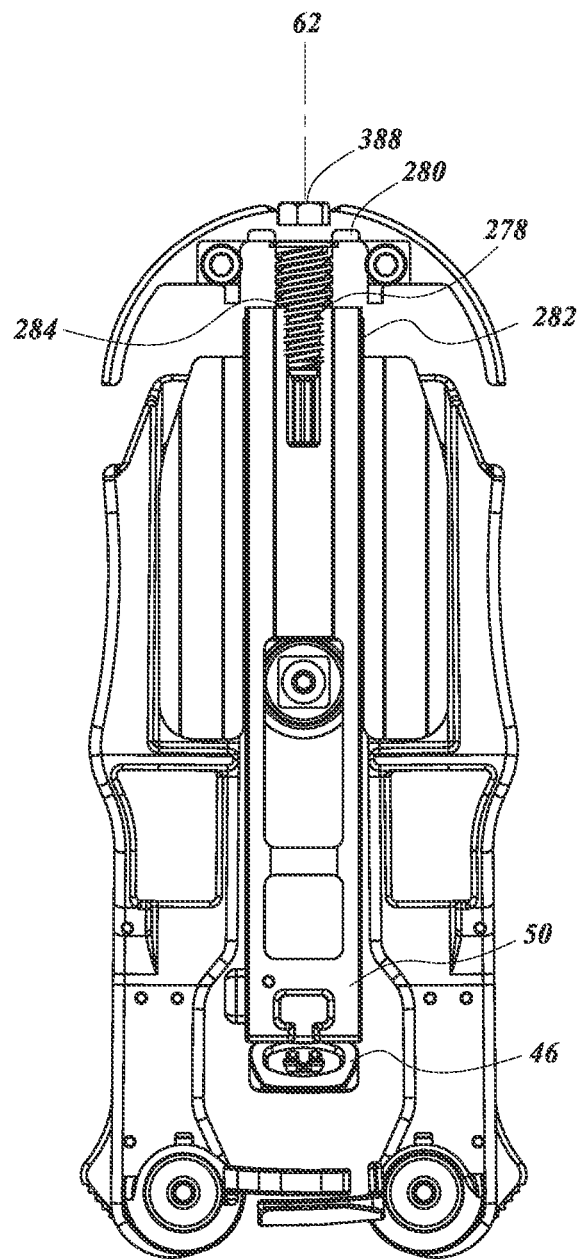
FIG. 18 provides an exploded view of a slide mechanism of FIG. 17.

FIGS. 17-18 depict an embodiment of slide mechanisms 28, 30. The retractor 10 can be in the "slid position," meaning that the first arm 12 and the second arm 32 are displaced in the proximal-distal direction relative to the third blade 46 along a sixth axis 62. The retractor 10 can be in the "slid position," meaning that the third blade 46 is displaced in the proximal-distal direction relative to the body 26 along a sixth axis 62. While the application uses the phrase "the slid position," it is understood that one or more positions may be described as slid. For instance, the first arm 12 can be slid at any position along the body 26, the second arm 32 can be slid at any position along the body 26, the third blade 46 can be slid at any position along the body 26, the first arm 12 can be slid approximately the same distance as the second arm 32, wherein the width in the slid position is greater than the incision width or the width of any of the blades 18, 38, 46, or other slid positions.

FIG. 16 depicts an embodiment of a slide mechanism 262 that provides an additionally degree of freedom. The slide mechanism 262 can include the carriage 264. The first arm 12 and the second arm 32 can be coupled to the carriage 264 via pins 294, 296, as described herein. The first arm 12, the second arm 32, and the carriage 264 can move as a unit relative to the body 26.

The carriage 264 can be attached to the body 26 via a track 266. In some embodiments, the track 266 can be linear and/or parallel to the width of the blades 18, 38, 46. The track 266 can extend from the proximal end of body 26 to the distal end of the body 26, or over a portion therewithin. The track 266 can define the sixth axis 62. A screw 274 can extend along the track 266. The screw 274 can be configured to mate with a bearing (not shown). The bearing allows the screw 274 to rotate without translation (e.g., rotate in place).

The slide mechanism 262 can include an outer cylinder 270. The outer cylinder 270 can include a threaded bore 272. The threaded bore 272 can couple with the screw 274. The outer cylinder 270 can be coupled to the carriage 264 such that translation of the outer cylinder 270 causes translation of the carriage 264. In some configurations, the outer cylinder 270 and the carriage 264 translate along the screw 274 as the screw 274 rotates.

The slide mechanism 262 can include an actuator 268 that permits the carriage 264, the first arm 12, and the second arm 32 to slide along the screw 274. The rotation of the actuator 268 can cause the outer cylinder 270 to translate along the screw 274. The translation of the outer cylinder 270 can cause the carriage 264, the first arm 12, and the second arm 32 to translate along the screw 274. The translation of the actuator 268 can cause the carriage 264, the first arm 12, and the second arm 32 to translate along the sixth axis 62.

Referring back to FIG. 11, the proximal end of the body 26 can include the actuator 268. In some embodiments, the actuator 268 can include an outer engagement 276 that abuts a proximal end of the body 26. The outer engagement 276 can include a plurality of flats designed to engage a driver. Other configurations are contemplated. Rotation of the outer engagement 276 causes the carriage 264 to translate from the proximal end of the body 26 toward the distal end of the body 26 along the sixth axis 62.

The slide mechanism 262 permits the arms 12, 32 to extend a greater distance from the distal end of the body 26. The slide mechanism 262 permits the first blade 18 and the second blade 38 to slide relative to the third blade 46. In the illustrated embodiment, the third blade 46 is not coupled to the slide mechanism 262. This permits the first blade 18 and the second blade 38 to slide relative to the third blade 46. The slide mechanism 262 permits the incision to be stretched along the width of the incision to create an opening width greater than width W". One skilled in the art will recognize that the carriage 264 can translate in either direction.

FIG. 16 also depicts an embodiment of a slide mechanism 278 that provides an additionally degree of freedom. The third blade 46 can be coupled to slide mechanism 278. The third blade 46 can be coupled to the slide mechanism 278 via the third arm 50. The third blade 46 and the third arm 50 can move as a unit relative to the body 26.

The third blade 46 can be attached to the body 26 via a track 280. In some embodiments, the track 280 can be linear and/or parallel to the width of the blades 18, 38, 46. The track 280 can extend from the proximal end of body 26 to the distal end of the body 26, or over a portion therewithin. A screw 286 can extend along the track 280. The screw 286 can be configured to mate with a bearing (not shown). The bearing allows the screw 286 to rotate without translation (e.g., rotate in place). The track 280 can define the sixth axis 62.

The slide mechanism 278 can include an outer cylinder 282. The outer cylinder 282 can include a threaded bore 284. The threaded bore 284 can mate with a screw 286. The outer cylinder 282 can be coupled to the third arm 50. In some configurations, the outer cylinder 282, the third arm 50, and the third blade 46 translates along the screw 286 as the screw 286 rotates.

The slide mechanism 278 can include an actuator 288 that permits the third arm 50 and the third blade 46 to slide along the screw 286. The rotation of the actuator 288 can cause the outer cylinder 282 to translate along the screw 286. The translation of the outer cylinder 282 can cause the third arm 50 and the third blade 46 to translate along the screw 286. In embodiments where the track 280 is along the sixth axis 62, the translation of the outer cylinder 282 can cause the third arm 50 and the third blade 46 to translate along the sixth axis 62.

Referring back to FIG. 11, the proximal end of the body 26 can include the actuator 388. In some embodiments, the actuator 388] can include an outer engagement 390 that abuts a proximal end of the body 26. The outer engagement 390 can include a plurality of flats designed to engage a driver. Other configurations are contemplated. Rotation of the outer engagement 390 causes the third arm 50 and the third blade 46 to translate from the proximal end of the body 26 toward the distal end of the body 26 along the sixth axis 62.

The slide mechanism 278 permits the third blade 46 to extend a greater distance from the distal end of the body 26. The slide mechanism 278 permits the third blade 46 to slide relative to the first blade 18 and the second blade 38. In the illustrated embodiment, the first blade 18 and the second blade 38 are not coupled to the slide mechanism 278. This permits the third blade 46 to slide relative to the first blade 18 and the second blade 38. The slide mechanism 278 permits the incision to be stretched along the width of the incision to create an opening width greater than width W". One skilled in the art will recognize that the third blade 46 can translate in either direction.

Figure 19:
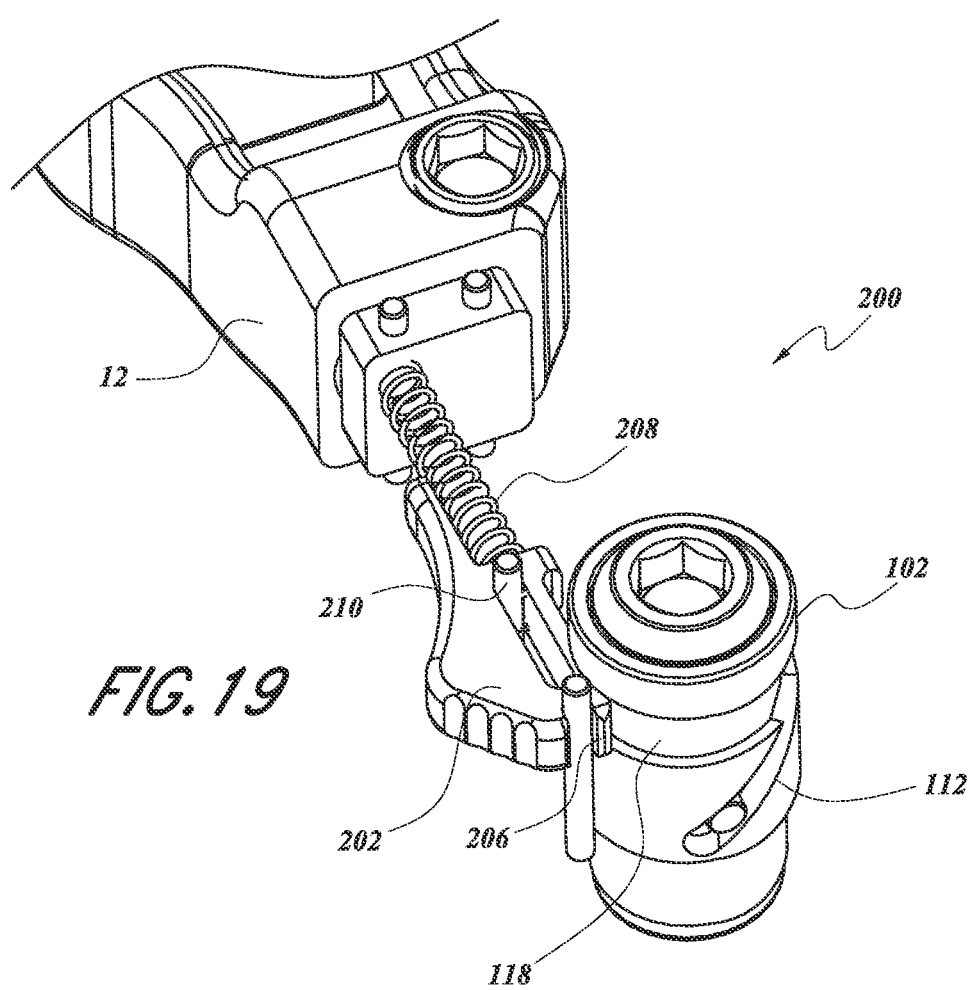
FIG. 19 provides an exploded view of a quick release mechanism of FIG. 1.

FIG. 19 illustrates a quick release mechanism 200. The first blade assembly 16 and the second blade assembly 36 can be removed from the retractor 10. The quick release mechanism 200 can include a first tab 202 associated with the first blade assembly 16 and a second tab 204 associated with the second blade assembly 36. The tabs 202, 204 can be located on the hubs 97, 98. The tabs 202, 204 can be located on the arms 12, 32. The tabs 202, 204 can be depressed thereby releasing the blade assemblies 16, 36. In some embodiments, the tabs 202, 204 can be independently actuated.

Referring back to FIGS. 12-13, the inner barrel 102 can have an engagement groove 118 circumscribing the inner barrel 102 above the slots 112, 114. The tab 202 can have an appropriately sized retention member 206 such as a flange which can be received within the groove 118. The retention member 206 allows the inner barrel 102 to rotate but not translate within the first connecting hole 100.

The tab 202 can be biased by a spring 208. The tab 202 can be retracted toward the body 26 to allow the inner barrel 102 to be inserted within the first connecting hole 100. The tab 202 can be released to engage the retention member 206 with the groove 118. The spring 208 can bias the retention member 206 toward the distal direction and into engagement with the groove 118. The blade assemblies 16, 36 can be inserted into the hubs 97, 98 from underneath the hubs 97, 98.

The first blade assembly 16 can include a first post 210 designed to be coupled to the first tab 202. The first post 210 can be an alignment post. The first post 210 can help facilitate alignment between the retention member 206 and the groove 118.

The arms 12, 32 may be removed from the body 26. For instance, in the illustrated embodiment, the pins 294, 296 can be removed to remove the arms 12, 32 from the body 26. This may occur at any time, e.g. prior to or during sterilization of the retractor 10 or during a surgical procedure once the retractor 10 has been opened. Removal of the body 26 during surgery may afford a member of the surgical team greater freedom of motion, an improved field of view or both.

The third blade 46 may be removed from the third arm 50. For instance, in the illustrated embodiment, the third arm 50 can have a mating configuration such as a snap fit with the third blade 46. The third blade 46 may be removed at any time, e.g. prior to or during sterilization of the retractor 10 or during a surgical procedure once the retractor 10 has been opened. Removal of the third blade 46 during surgery may afford a member of the surgical team greater freedom of motion, an improved field of view or both.

Some embodiments contemplate kits comprising a retractor 10. In some embodiments, the kit comprises a plurality of removable and exchangeable blade assemblies 16, 36 and/or blades 18, 38, 46. Each kit may comprise a different actuator, a different rotation mechanism, a different pivot mechanism, a different spread mechanism, and/or a different slide mechanisms. Each blade assembly may comprise a different blade. In some embodiments, the kit comprises at least three blade assemblies having amongst the three blade assemblies at least two distinct blade configurations. In other embodiments, the kit comprises from 3 to 12 blade assemblies having amongst the several blade assemblies from 2 to 12 distinct blade configurations. In some embodiments, the kit comprises at least two pairs of identical, substantially similar, or mirror image blade assemblies. In some embodiments, the kit comprises at least two pairs of mirror image blade assemblies. In other embodiments, the kit comprises from 2 to 10, especially about 2 to 5 such pairs of blade assemblies.

In some embodiments, the retractor 10 may be provided to a surgeon or surgical personnel in the form of a kit comprising additional surgical articles and optionally instructions for the use and handling of the retractor. Such additional surgical articles may include one or more of: scalpels, suture needles, pedicle screws, suture material, spinal implant material, spinal fusion rods, biocompatible adhesive and closure staples.

In some embodiments, the blades 18, 38, 46 are removable. In some embodiments, the blades 18, 38, 46 may take on a variety of shapes and sizes. In some embodiments, a kit is provided comprising a plurality of retractors having blades of various sizes, shapes or both. In some embodiments, a kit is provided comprising one or more arms and two or more blade assemblies (optionally of varying blade sizes and/or shapes). In some embodiments, a kit is provided comprising a retractor, optionally more than two blades assemblies, at least two of which differ from one another in size, shape or both, and one or more pedicle screws for performing lumbar surgery. Thus, a variety of surgical kits for performing surgery, especially back surgery, are contemplated and methods of using the retractor to perform surgery, especially back surgery, are contemplated.

The retractor 10 described herein can allow the blades 18, 38, 46 to pivot and swing open as described herein. The movement of the blades 18, 38, 46 can cause less trauma to the tissue by gently pushing the tissue apart. The blades 18, 38, 46 can have a low profile configuration that can cause less trauma upon insertion. The blades 18, 38, 46 can be moved about a variety of axes to reduce trauma. The blades 18, 38, 46 can be independently actuated to reduce trauma.

FIG. 20 illustrates the attachment mechanism 15. The attachment mechanism 15 can be located on the body 26. The attachment mechanism 15 couples the body 26 to a fixture (not shown). The fixture can be a support arm. The fixture can be located within the operating arena. The fixture can support the body 26 during the procedure.

The attachment mechanism 15 can include features to enable coupling to the fixture. The attachment mechanism 15 can be threaded. The attachment mechanism 15 can include a serrated plate to limit rotation. The attachment mechanism 15 can include any features to ensure a stable connection between the fixture and the body 26.

On the market retractor systems typically have two attachment points. A first attachment point allows the outer blades to move relative to the first attachment point. A second attachment point allows another blade, for instance, a middle blade to move relative to the second attachment point. With the on the market retractor systems, the retractor can lose the surgical site when changing attachment points. The retractor can shift when removed from the attachment point and switched to another attachment point.

FIG. 20 illustrates a single attachment point located at the attachment mechanism 15 for the body 26. The first blade 18 and the second blade 38 can move relative to the one attachment point. For instance, the first blade 18 and the second blade 38 can pivot with the pivot mechanisms 22, 42 relative to the attachment point. The first blade 18 and the second blade 38 can rotate with the rotation mechanism 20, 40 relative to the attachment point. The first blade 18 and the second blade 38 can spread with the spread mechanism 34 relative to the attachment point. The first blade 18 and the second blade 38 can slide with the slide mechanism 28 relative to the attachment point.

The third blade 46 can also move relative to the one attachment point. The third blade 46 can slide with the slide mechanism 30 relative to the attachment point. The third blade 46 can pivot relative to the attachment point. Each of the blades 18, 38, 46 can move independently of the attachment point. Each of the blades 18, 38, 46 can move independently of the body 26.

The one attachment point located at the attachment mechanism 15 can provide more stability and accuracy during retraction. The one attachment point can maintain the position of the retractor 10 during the procedure. The surgeon does not need to switch between attachment points to allow operation of the blades. Each blade can be manipulated when the body 26 is coupled to the fixture via the attachment mechanism 15. In some methods of use, the body 26 is not removed from the attachment mechanism during the course of the procedure. In some methods of use, there is no need to find the surgical site or reposition the retractor after switching attachment points.

Figure 21A:
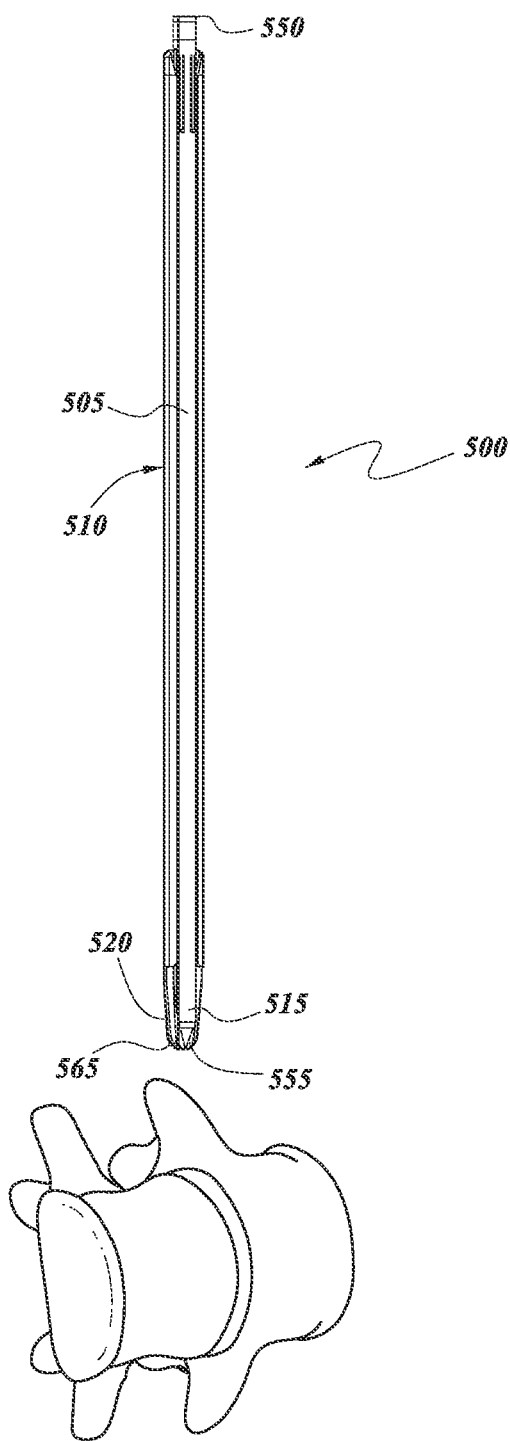

FIG. 21A-21E illustrates a probe system 500 and a method for its use in conjunction with the retractor 10. The probe system 500 can include one or more probes. The probe system 500 can include one probe, two probes, three probes, four probes, etc. In FIG. 21A, the probe system 500 includes an anterior probe 505 and a posterior probe 510. The probes 505, 510 can form a shape having a smooth perimeter. The smooth perimeter can form a generally flat shape such as a shape having two or more generally flat sides. In some embodiments, each probe 505, 510 forms an equal half of the perimeter. In some embodiments, the posterior probe 510 forms greater than half of the perimeter. The anterior probe 505 faces toward the front of the system (e.g., distal end when coupled to the retractor 10) and the posterior probe 510 faces toward the rear of the system (e.g., proximal end when coupled to the retractor 10).

In some embodiments, the anterior probe 505 includes an anterior electrode 515. In some embodiments, the posterior probe 510 includes a posterior electrode 520. The electrodes 515, 520 can be on an exterior surface of the probes 505, 510. The electrodes 515, 520 can be on a distal surface of the probes 505, 510. The electrodes 515, 520 can face outward from the probes 505, 510. The electrodes 515, 520 can be positioned at any radial distance (e.g., 90 degrees apart, 100 degrees apart, 110 degrees apart, 120 degrees apart, 130 degrees apart, 140 degrees apart, 150 degrees apart, 160 degrees apart, 170 degrees apart, 180 degrees apart, etc.). In some embodiments, the electrodes 515, 520 are on opposed surfaces. The anterior electrode 515 can monitor the anterior side of the probes 505, 510 and the posterior electrode 520 can monitor the posterior side of the probes 505, 510.

The posterior probe 510 can include a mating configuration with the anterior probe 505. The mating configuration can be a tongue and groove configuration. In some embodiments, the posterior probe 510 can include a groove 530 and the anterior probe 505 can include a tongue 525. The proximal end of the posterior probe 510 can accept the anterior probe 505. In some methods of use, the anterior probe 505 is aligned with the posterior probe 510. In some methods of use, the anterior probe 505 is slid down the length of the posterior probe 510 from a first end 550 of the posterior probe 510 toward a second end 555 of the posterior probe. In some methods of use, the anterior probe 505 is slid until the anterior electrode 515 aligns with the posterior electrode 520. The structure of the probes 505, 510 when coupled together can facilitate its passage through tissues of a patient (e.g., psoas muscles) which can run parallel to the flat surfaces of the probes 505, 510. For example, the generally flat shape of the probes 505, 510 can dissect and/or dilate the tissues of a patient by separating the psoas muscle along the muscle fibers in a lateral approach to the spine. The flat surfaces of the probes 505, 510 can be oriented parallel to (i.e., aligned with) the lengths of the muscle fibers, which helps to minimize trauma to the muscle tissue as the probes are inserted through the psoas muscle.

The posterior probe 510 can include a retention configuration with the anterior probe 505. The retention configuration can maintain the position of the anterior probe 505 relative to the posterior probe 505. In some embodiments, the retention configuration is a stop coupled to the posterior probe 510. The anterior probe 505 abuts the stop thereby limiting further distal movement. In some methods of use, the anterior probe 505 is slid down the length of the posterior probe 510 until the anterior probe 505 abuts a stop.

The mating configuration can couple other components of the probe system 500 with the probes 505, 510. The probe system 500 can include a shim 535. In some embodiments, the posterior probe 510 can include the groove 530 and the shim 535 can include a tongue 540. The first end 550 of the posterior probe 510 can accept the shim 535. In some methods of use, the shim 535 is aligned with the posterior probe 510. In some methods of use, the shim 535 is slid down the length of the posterior probe 510 from the first end 550 of the posterior probe 510 toward the second end 555 of the posterior probe 510. In some embodiments, the shim 535 is configured to couple with the third blade 46 instead of, or in addition to the posterior probe 510.

In some embodiments, the third blade 46 can include the slot 48. The slot 48 is sized to accept one or more probes 505, 510. In some embodiments, the slot 48 is sized to accept the anterior probe 505 coupled to the posterior probe 510. The slot 48 is sized to accept the shim 535. As described herein, the posterior probe 510 can form greater than half of the perimeter of the assembled probes 505, 510. The slot 48 can limit motion of the posterior probe 510 in directions other than translation. The slot 48 can limit motion of the posterior probe 510 after the anterior probe 505 is removed. The slot 48 can limit motion of the posterior probe 510 after the shim 535 is inserted.

The probes 505, 510 can be inserted underneath the third blade 46. The third blade 46 can be inserted underneath the third arm 50. In some methods of use, the probes 505, 510 are aligned with the third blade 46. In some methods of use, the third blade 46 is slid down the length of the probes 505, 510 from the first end 550 of the probes 505, 510. The slot 48 of the third blade 46 can fit substantially closely around the probes 505, 510.

The retractor 10 can include a retention configuration with the shim 535. The retention configuration can maintain the position of the retractor 10 relative to the shim 535. In some embodiments, the retention configuration is one or more notches 540 located on the third blade 46. The shim 535 includes a corresponding detent 545 that engages one or more notches 540 thereby limiting further movement of the shim 535. In some methods of use, the shim 535 is slid down the length of the third blade 46 engaging and disengaging the one or more notches 540 on the third blade 46. The one or more notches 540 can be in discrete positions along the third blade 46. In some embodiments, the engagement between the detent 545 and the notches 540 provides feedback such as an audible click or tactile feedback for the user. Other retention configurations are also contemplated, such as ratcheting hooks, releasable clamps, and the like.

In some embodiments, the shim 535 is shorter than one or more probes 505, 510. In some methods of use, the shim 535 retains the retractor 10 at the anchorable location instead of the probes 505, 510. The shorter length of the shim 535 as compared to the probes 505, 510 can provide clearance around the retractor 10 for the user to work. In some methods of use, the shim 535 is held by the third blade 46 during use.

Each probe 505, 510 can have a probe body extending between the first end 550 and the second end 555. The second end 555 can include a tip 565 for insertion within the anchorable location. In some embodiments, the second end 555 can include a distal shoulder 570. The distal shoulder 570 can limit penetration of the probe 505, 510. In modified embodiments, the probe 505, 510 can have a distal end of a different shape. For example, the probe 505, 510 can be formed without the shoulder 570 and/or without the tip 565 and/or one of both elements can be modified in shape.

In some embodiments, probe 505, 510 coupled together can be rectangular in horizontal cross section (i.e., the plane bisecting the probe 505, 510 perpendicular to the axis formed by the first end 550 and the second end 555). In other embodiments, the probe 505, 510 coupled together can be circular in horizontal cross section or oval in horizontal cross section. Some representative cross sectional shape the probes 505, 510 coupled together can include: a circle; an oval; a triangle; a flattened oval; a thin flattened oval; a rounded rectangle; a thin rounded; a rectangle; and a thin rectangle. Each probe 505, 510 can form a portion of the cross section, for instance half of the cross section. In yet other embodiments, the probe 505, 510 can be any other appropriate shape, including but not limited to square, triangular, and ellipsoid. A rectangular cross-sectional shape can include a shape in which the corners of the device are rounded and/or arrangements in which the adjacent sides are not exactly perpendicular (e.g., plus or minus 10 degrees, 5 degrees, 1 degrees or 0.1 degrees from perpendicular) and/or when the sides of the probe have ridges, bends that deviate 10%, 5%, 1% or 0.1% from the width or length of a side. FIG. 21A-21D illustrate the probes 505, 510 which together form an oval cross section.

In some embodiments, the probes 505, 510 can be constructed out of a biocompatible metal, such as but not limited to stainless steel, titanium, and cobalt chrome moly. In other embodiments, the probes 505, 510 can be constructed out of a biocompatible ceramic. In still other embodiments, the probes 505, 510 can be constructed out of any stiff, biocompatible material, including such classes of materials as metals, ceramics, and polymers, or any combinations thereof. In some embodiments, the probes 505, 510 can be constructed out of non-biocompatible material and coated with a biocompatible material.

In some embodiments, the probes 505, 510 can have a vertical dimension (i.e., between ends 550, 555) in the range of about 5-50 cm, about 6-40 cm, about 7-30 cm, about 7-20 cm and about 8-10 cm or any other range which is appropriate to allow the probes 505, 510 to function as desired. In some embodiments, the probes 505, 510 can have a width in its largest, non-vertical dimension, in the range of about 5 mm-5 cm, about 6 mm-4 cm, about 7 mm-3 cm, and about 8 mm-2 cm, including about 1.5 cm.

In some embodiments, the shoulders 570 can extend horizontally in from the edges of the probes 505, 510 in the range of about 0.1-5 mm, about 0.2-4 mm, about 0.3-3 mm, about 0.4-2 mm, about 0.5-1 mm, and about 0.6-0.8 mm. In some embodiments, the external corners where the shoulders 570 meet the vertical edges of the probes 505, 510 can be squared. In other embodiments, the external corners where the shoulders 570 meet the vertical edges of the probes 505, 510 can be rounded or smoothed. In some embodiments, the shoulder 570 can be machined flat on the bottom (particularly in such embodiments in which the probe 400 is a shape other than rectangular). In other embodiments, the shoulder 570 can be sharpened across their entire length to form a blade along their entire length. In other embodiments, the shoulders 570 can be are sharpened across only a portion of their length to form a blade along only a portion of their length. For example, in some embodiments, only half of each shoulder 570 is sharpened (e.g., either the half of the shoulders 570 abutting the tip 565 or the half of the shoulders 570 abutting the edges of the probes 505, 510).

In some embodiments, the tip 565 can extend downward from the probes 505, 510. In some embodiments, the tip 565 can be substantially triangular. In other embodiments, the tip 565 can be substantially parabolic. In other embodiments, the tip 565 can be a small cylindrical member, such as a trocar. In yet other embodiments, the tip 565 can be any shape which allows anchoring of the probes 505, 510 in tissue. In some embodiments, the edges of the tip 565 can be machined to be substantially smooth. In other embodiments, the edges of the anchor tip 565 can be sharpened to form a blade.

In some embodiments, at least a portion of the vertical edges of the probes 505, 510 can be sharpened. In some of these embodiments, the portion of the edges of the probes 505, 510 which are sharpened can be disposed near the second end 555 of the probes 505, 510. As a representative example, 1-5 cm of the edges of the probes 505, 510 extending up from the second end 555 and distal shoulders 570 can be sharpened to form a blade to facilitate insertion of the probes 505, 510 into corporeal tissue of a patient.

The probe system 500 illustrated in FIG. 21A is a thin, blade like probe having a flat cross-section. The flat cross-section may limit the probes 505, 510 ability to be rotated within the anchorable location to detect nerve signals. In some embodiments, each probe 505, 510 includes an electrode 515, 520 to detect nerve signals. The electrodes 515, 520 can be positioned to detect nerve activity at locations approximately 180 degrees apart. The structure of the probes 505, 510 can facilitate its passage through tissues of a patient (e.g., psoas muscles) which can run parallel to the flat surfaces of the probe.

In operation, a physician can select a location in which he desires to use a retractor 10 to form an operative channel in the tissues of the patient (the spine will be used in this example for illustration purposes only). A location is preferably selected that provides adequate access to an intervertebral disc space, yet minimizes the risk of injury to the nerves extending from the intervertebral foramen. After the surgeon selects the location for retractor 10 placement, he can make an incision in the skin and insert one or more of the probes 505, 510 by placing the tip 565 against the surface of the patient. In some methods of use, the probes 505, 510 are coupled prior to insertion. The surgeon applies pressure to the first end 550 of one or more probes 505, 510. The physician can then continue to apply pressure, thereby pushing the one or more of the probes 505, 510 through the tissue of the patient, until the probes 505, 510 are fully in place. In some embodiments, an imaging modality can be used during the insertion of the one or more probes 505, 510. As a representative, non-limiting example, X-ray fluoroscopy can be used during insertion of the one or more probes 505, 510 to ensure correct placement. Any appropriate imaging modality can be used to monitor the placement of the one or more probes 505, 510. In some embodiments, a surgeon can make an incision with another instrument, such as a scalpel, prior to the insertion of the one or more probes 505, 510, into which the one or more probes 505, 510 is inserted. In some embodiments, a K-wire (i.e., guide wire) can first be anchored at the location for retractor 10 placement. One or more probes 505, 510 can have a passage extending through its longitudinal length to receive the K-wire when the one or more probes 505, 510 are inserted at the surgical location. The K-wire advantageously provides improved accuracy in placement of the one or more probes 505, 510 and can also help stabilize the one or more probes 505, 510 during insertion through the patient tissue.

Figure 21B:
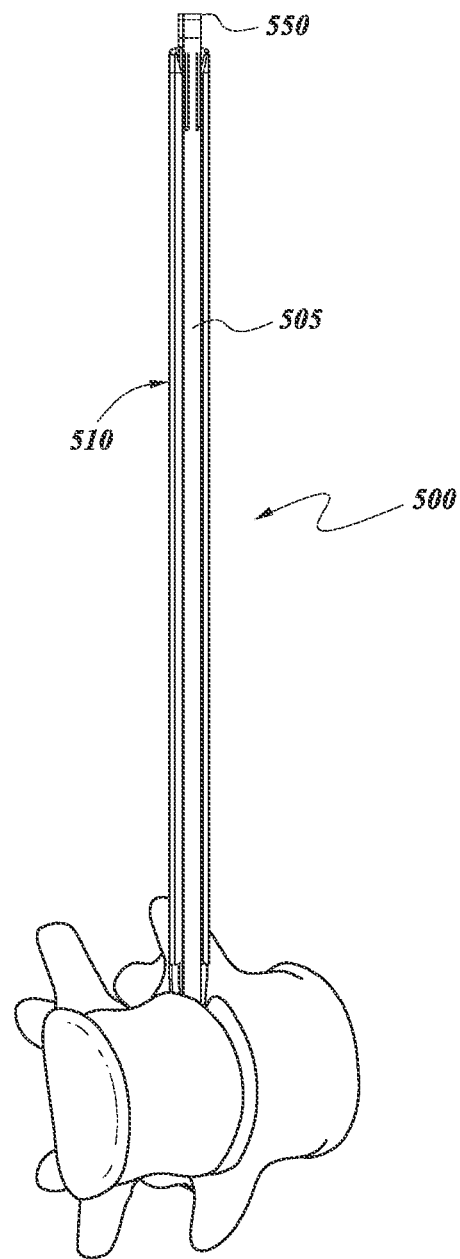

FIG. 21B illustrates the probes 505, 510 fully in place in a patient. The probes 505, 510 have been inserted into the side of the spinal column (here defined by a first vertebra 440, a second vertebra 450, and the disc 460 between them). FIG. 21B illustrates the placement of the probe 400 in a location in which the tip 565 can anchor the probes 505, 510. As shown in FIG. 21B, the probes 505, 510 have been inserted into the patient until the tip 565 has sunk at least some distance into the disc 460 between the first vertebra 440 and second vertebra 450. The tip 565 has sunk into the disc 460 up until the shoulders 570 of the probes 505, 510. The shoulders 570 serve in this example to limit the possible insertion depth of the tip 565 of the probe 570.

FIG. 21C illustrates the third blade 46 of the retractor 10 (as disclosed herein) and a placed probes 505, 510. The third blade 46 can include a longitudinally extending slot 48 sized to accept the probes 505, 510. The third blade 46 can fit substantially closely around the probes 505, 510. The third blade 46 can be any type of blade as described above, including but not limited to a substantially flat blade. An incision I having a length L is made in a suitable tissue, such as the skin overlying or in proximity to the lumbar region of the spine.

FIG. 21D illustrates the shim 535 and the placed third blade 46 of the retractor 10 and placed probes 505, 510. The third blade 46 can include the slot 48 sized to accept the shim 535 after the anterior probe 505 is removed. The third blade 46 can fit substantially closely around the shim 535 and the posterior probe 510.

FIG. 21E illustrates the first blade 18 and the second blade 38 of the retractor 10 in their closed configuration placed near the third blade 46. The blades 18, 38, 46 will be in their stacked configuration when coupled. The blades 18, 38, 46 are in the closed position and aligned relatively parallel to one another. The third arm 50 of the third blade 46 can couple with the body 26. FIG. 21E shows the retractor 10 still in the closed position.

In some methods, the retractor 10 of FIG. 21E is manipulated to achieve the opened position, as shown and described in FIGS. 4-5 and 10. In the opened position, the incision can be stretched along the length of the incision to pull open the incision. In some methods of use, translation about the third axis 56 results in the retractor 10 opening: i.e. the first blade 18 and the second blade 38 move apart from one another in the general directions of directional arrows B, C, respectively. The incision can be stretched open in the direction of the directional arrows B and C so that it obtains a length L' greater than length L of the incision.

In some methods, the retractor 10 of FIG. 21E is manipulated to achieve the rotated position, as shown and described in FIGS. 6-7 and 12-14. In the rotated position, the incision can be stretched along the width of the incision. Turning the rotation mechanism 20, 40 in the direction of the arrows D and E about the first axis 52 and the second axis 54, respectively results in the rotating of the first blade 18 and the second blade 38 respectively, resulting in the widening of the incision. The aperture can be opened to a width W'. If the retractor is previously opened as shown in FIG. 4-5, then the aperture would provide an access area of dimensions L' by W' for surgical personnel to view the operating field, to pass instruments, sutures, implants and other surgical materials through the aperture.

In some methods, the retractor 10 of FIG. 21E is manipulated to achieve the pivoted position, as shown and described in FIGS. 8-9 and 15-16. In the pivoted position, the incision can be stretched along the width and/or length of the incision. Turning the pivot mechanism 22, 42 pivots the first blade assembly 16 and second blade assembly 36 in the direction of the arrows H and I about the fourth axis 58 and the fifth axis 60, respectively results in the pivoting of the first blade 18 and the second blade 38, further stretching the incision. The aperture can be opened to a length L" and a width W". The aperture can provide an access area of dimensions L" by W" for surgical personnel to view the operating field, to pass instruments, sutures, implants and other surgical materials through the aperture.

In some methods, the retractor 10 of FIG. 21E is manipulated to achieve the slid position, as shown and described in FIGS. 17-18. In the slid position, the incision can be stretched along the width of the incision. Moving the slide mechanism 262 results in the translation of the arms 12, 32, and therefore the translation of the blades 18, 38, causing the incision to open. Moving the slide mechanism 278 results in the translation of the third blade 46, causing the incision to open. The aperture A can be opened to a width wider than width W".

Reversal of the steps described above results in a final incision having substantially the same length L and essentially no width, like the original incision. By way of comparison, in order for a prior art device having a pair of blades to create such an aperture, the incision would have to have a length L' or L" and the blades would have to have a width of W' or W". The present retractor 10 permits the use of a much smaller incision to create the aperture. The present retractor 10 permits less invasive surgical methods, quicker and more comfortable recovery from surgery and potentially cost savings for the medical coverage provider.

The probes 505, 510 can be removed prior to any of these steps or left in place during the procedure. The probes 505, 510 can allow a surgeon to easily and quickly insert a retractor 10 without cutting an incision all the way to the surgery site prior to inserting the retractor 10 into the desired location to access the surgery site. Rather, the surgeon can quickly and easily insert the probes 505, 510 into the desired location, anchor the probes 505, 510 using the tip 565 in the desired location, slip the third blade 46 of the retractor 10 around one or more of the probes 505, 510, and then simply slip the retractor 10 into place. From this position, the first blade 18 and/or the second blade 38 can be moved in any of the ways described herein. From this position, the first arm 12 and the second arm 32 can be moved in any of the ways described herein.

In some embodiments, the probes 505, 510 comprise at least one electrode 515, 520, wherein the at least one electrode 515, 520 is capable of stimulating a nerve to provoke an electromyographic response in the nerve. The probes 505, 510 can sense nerve activity as a probe and anchor the retractor 10 at an anchorable location. In some embodiments, the first end 550 of the probes 505, 510 can be broken off once the second end 555 of the probes 505, 510 is implanted. The probes 505, 510 can have one or more break points along the length of the probes 505, 510 to facilitate this break. The break points can provide clearance around the retractor 10 for the user to work.

In some embodiments, only one electrode is used. In other embodiments, a plurality of electrodes can be used, including about 1-10 electrodes, about 2-8 electrodes, about 3-6 electrodes and about 4-5 electrodes. In some embodiments, at least one electrode can be disposed on the tip 565. In some embodiments, at least one electrode can be disposed on the probes 505, 510. The electrode 515, 520 can be included in any of the embodiments described herein.

In some embodiments, the probe system 500 comprises an endoscope 499, wherein the endoscope 499 can comprise an imaging element 432 at the distal end 412 of the endoscope 499. In some of these embodiments, the endoscope 499 can be configured to both allow a surgeon to visualize the placement of the probe system 500 as well as allow a surgeon to slide a retractor 10 down over the probe system 500 and into place as described herein to create an operative channel. In some embodiments, the endoscope 499 can include a tip. Such an endoscope can be applied to any of the embodiments described herein.

The method of use can include any step described herein. In some methods of use, the probe system 500 can facilitate placement of the retractor 10 relative to an anatomical feature of the patient. The probe system 500 can be used on a portion of the spine including a first vertebra 440, a second vertebra 450, and a disc 460 disposed between the first vertebra 440 and the second vertebra 450, as shown in FIGS. 21A-21B. FIG. 21A illustrates the probes 505, 510 being inserted into a patient (not fully shown) toward the spine (only a first vertebra 440, second vertebra 450, and disc 460 are illustrated in this representative example). In some methods of use, an incision is made on the patient. In some methods of use, the anterior probe 505 and the posterior probe 510 are inserted into a patient, preferably into an anchorable location, such as a collagenous tissue, bone, or vertebral disc. In some methods of use, the posterior probe 510 and the anterior probe 505 are coupled with the mating configuration prior to insertion within the patient. The probes 505, 510 are inserted while assembled together. In some methods of use, the posterior probe 510 is inserted first. The anterior probe 505 is slid along the length of the posterior probe 510 toward the anchorable location.

In some methods of use, one or more probes 505, 510 includes an electrode 515, 520 to monitor the patient. In some embodiment, each probe 505, 510 includes an electrode 515, 520. In some methods of use, each electrode 515, 520 monitors nerve activity. In some methods of use, the electrodes 515, 520 monitor nerve activity in opposite directions. In some methods of use, the electrodes 515, 520 monitor nerve activity in directions 180 degrees apart.

In some methods of use, the probes 505, 510 are secured to the disc 460. In some methods of use, a K-wire is inserted and attached to the disc 460. In some embodiments, a K-wire (i.e., guide wire) can first be anchored at the location for retractor 10 placement. One or more of the probes 505, 510 can have a passage extending through its longitudinal length to receive the K-wire when the probes 505, 510 are inserted at the surgical location. The K-wire advantageously provides improved accuracy in placement of the probes 505, 510 and can also help stabilize the probes 505, 510 during insertion of the retractor blades through the patient tissue.

In some methods of use, one or more blades of the retractor 10 are inserted over the probes 505, 510. In some methods of use, one or more blades of the retractor 10 are inserted over the probes 505, 510 after the probes 505, 510 are secured to the anatomy. In some methods of use, the third blade 46 of the retractor 10 is slid around the probes 505, 510. The third blade 46 can be slid from the first end 550 of the probes 505, 510 toward the second end 555 of the probes 505, 510. In some methods of use, the first blade 18 and the second blade 38 of the retractor 10 are placed in their closed configuration. The third blade 46 can be coupled to the third arm 50 underneath the body 26. The blades 18, 38, 46 will be in their stacked configuration when coupled.

In some methods of use, the anterior probe 505 is removed from the anchorable location. In some methods of use, the anterior probe 505 is removed after the retractor 10 is inserted over the probes 505, 510. In some methods of use, the anterior probe 505 is slid toward the first end 550 of the posterior probe 510. In some methods of use, the retractor 10 remains coupled to the posterior probe 510 after the anterior probe 505 is removed.

In some methods, the shim 535 is inserted into the anchorable location. In some methods of use, the shim 535 is inserted after the anterior probe 505 is removed. In some methods of use, the shim 535 is slid along the length of the posterior probe 510 toward the anchorable location. In some embodiments, the shim 535 engages the mating configuration of the posterior probe 510. In some methods of use, the shim 535 engages the third blade 46. In some methods of use, the detent 345 of the shim 535 engages one or more notches 340 of the third blade 46. In some methods of use, the notches 340 retain the shim 535 in a desired position relative to the third blade 46.

In some methods of use, the posterior probe 510 is removed from the anchorable location. In some methods of use, the posterior probe 510 is removed after the shim 535 is inserted into the anchorable location. In some methods of use, the K-wire or other securing device is removed from the anchorable location. In some methods of use, the K-wire or other securing device is removed after the shim 535 is inserted into the anchorable location.

In some methods of use, the third blade 46 remains coupled to the shim 535 during use. In some methods of use, the third blade 46 remains at the anchorable location during use.

The shim 535 can allow a surgeon to easily and quickly insert a retractor 10 without cutting an incision all the way to the surgery site prior to inserting the retractor 10 into the desired location to access the surgery site. Rather, after the third blade 46 is inserted over the probes 505, 510, the surgeon can quickly and easily insert the shim 535 onto the third blade 46 of the retractor 10 into the desired location, and then simply slip the first blade 18 and second blade 38 of the retractor 10 into place. From this position, the first blade 18 and/or the second blade 38 can be moved in any of the ways described herein. From this position, the first arm 12 and the second arm 32 can be moved in any of the ways described herein. The probes 505, 510 can be removed prior to any of these steps or left in place during the procedure.

The probe system 500 can be more accurate than other systems in maintaining the position of the surgical site. The probe system 500 can have small tolerances between components of the probe system 500. The posterior probe 510 is inserted at an anchorable location, as described herein. The probes 505, 510 find and monitor the surgical site with one or more electrodes 515, 520. The K-wire secures the surgical site. The posterior probe 510 can include a lumen to accept a K-wire therethrough. The inner diameter of the lumen can closely match the outer diameter of the K-wire to limit movement between the K-wire and the posterior probe 510.

The probes 505, 510 can have a mating configuration. The mating configuration can limit movement between the anterior probe 505 and the posterior probe 510 in directions other than translation. The combination of the K-wire and one or more probes 505, 510 can maintain the position of the surgical site.

The interaction between the slot 48 of the third blade 46 and the posterior probe 510 can maintain the position of the surgical site. There is little movement between the probes 505, 510 and the slot 48. The posterior probe 510 can be greater than half of the perimeter of the slot 48. The inner diameter of the slot 48 can closely match the outer diameter of the posterior probe 510 to limit movement between the slot 48 and the posterior probe 510 in a direction other than translation. The inner diameter of the slot 48 can closely match the outer diameter of the posterior probe 510, alone or when mated with the anterior probe 505 or the shim 535.

As described herein, there is little movement between the K-wire and the probes 505, 510. As described herein, there is little movement between the posterior probe 510 and the slot 48. As described herein, there is little movement between the probes 505, 510 and the slot 48. As described herein, there is little movement between the posterior probe 510 coupled to the shim 535 and the slot 48. This limitation of movement can limit the shifting of the retractor 10 from the surgical site.

While certain embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

Further features of this disclosure are given in the following numbered clauses:

Clause 1. A retractor comprising:
    a first blade,
    a first rotation mechanism that rotates the first blade about a first axis,
    a second rotation mechanism that rotates the second blade about a second axis,
    a first pivot mechanism that pivots the first blade about a fourth axis, wherein the fourth axis is skewed to the first axis;
    a second pivot mechanism that pivots the second blade about a fifth axis, wherein the fifth axis is skewed to the second axis.

Clause 2. The retractor of clause 1, wherein the first and second axes are substantially coplanar with one another.

Clause 3. The retractor of clause 2, wherein the first and second axes are coplanar with one another.

Clause 4. The retractor of clause 1, further comprising an actuator that translates the first blade and second blade about a third axis.

Clause 5. The retractor of clause 4, wherein the third axis is substantially perpendicular to the first axis, the second axis or both the first and second axes.

Clause 6. The retractor of clause 4, wherein the third axis is substantially perpendicular to both the first axis and the second axis.

Clause 7. The retractor of clause 4, wherein the third axis is perpendicular to the first axis, the second axis or both the first and second axes.

Clause 8. The retractor of clause 4, wherein the third axis is perpendicular to both the first and second axes.

Clause 9. The retractor of clause 4, further comprising a device for locking the first and second blades in at least one predetermined position along the third axis.

Clause 10. The retractor of clause 1, further comprising an actuator that slides the first blade and second blade about a sixth axis.

Clause 11. The retractor of clause 10, wherein the sixth axis is substantially perpendicular to the first axis, the second axis or both the first and second axes.

Clause 12. The retractor of clause 10, wherein the sixth axis is substantially perpendicular to both the first axis and the second axis.

Clause 13. The retractor of clause 10, wherein the sixth axis is perpendicular to the first axis, the second axis or both the first and second axes.

Clause 14. The retractor of clause 10, wherein the sixth axis is perpendicular to both the first axis and the second axis.

Clause 15. The retractor of clause 10, wherein the sixth axis is substantially parallel to the fourth axis, the fifth axis or both the fourth and fifth axes.

Clause 16. The retractor of clause 10, wherein the sixth axis is substantially parallel to both the first axis and the second axis.

Clause 17. The retractor of clause 10, wherein the sixth axis is parallel to the fourth axis, the fifth axis or both the fourth and fifth axes.

Clause 18. The retractor of clause 10, wherein the sixth axis is parallel to both the first axis and the second axis.

Clause 19. The retractor of clause 10, further comprising a device for locking the first and second blades in at least one predetermined position along the sixth axis.

Clause 20. The retractor of clause 1, further comprising an actuator that translates the first blade and second blade about a third axis and an actuator that slides the first blade and second blade about a sixth axis.

Clause 21. The retractor of clause 20, wherein the sixth axis is substantially perpendicular to the third axis.

Clause 22. The retractor of clause 20, wherein the sixth axis is perpendicular to the third axis.

Clause 23. The retractor of clause 20, further comprising a device for locking the first and second blades in at least one predetermined position along the sixth axis.

Clause 24. The retractor of clause 1, further comprising a third blade that remains stationary during movement of the first blade and the second blade.

Clause 25. The retractor of clause 24, wherein the first and third blades are of different sizes in at least one dimension.

Clause 26. The retractor of clause 24, wherein at least one of the first, second and third blades is a flat blade.

Clause 27. The retractor of clause 1, further comprising a third blade and a third pivot mechanism that pivots the third blade about a seventh axis, wherein the seventh axis is skewed to the fourth axis.

Clause 28. The retractor of clause 1, wherein at least one blade is removable.

Clause 29. The retractor of clause 1, wherein the first and second blades are removable.

Clause 30. A retractor blade assembly, comprising:
a first blade having attached thereto a first barrel, the first barrel having a wall and defining a first lumen, a first slot in the wall having a first slope,
a first screw having an axis, the first screw fitting within the first lumen of the first barrel
a collar having an inner surface configured to mate with the outer surface of the first screw, the collar having a hole that aligns with the first slot in the wall of the first barrel;
a connecting pin fitting through the hole and the slot such that movement of the collar along the axis causes the first barrel to rotate in a first direction; and
a hub comprising a first connecting hole, wherein the first barrel fits within the first connecting hole.

Clause 31. The blade assembly of clause 30, wherein the hub is adapted to be removably affixed to an arm of a retractor.

Clause 32. The blade assembly of clause 30, wherein the hub comprises a second connecting hole and a third connecting hole, wherein the retractor blade assembly further comprises a second screw configured to be received within the third connecting hole, a pin configured to be received within the second connecting hole, wherein movement of the second screw causes the hub to rotate about a post.

Clause 33. A retractor blade assembly, comprising:
a first blade having attached thereto a first barrel,
a hub having a second connecting hole and a third connecting hole,
a second screw configured to be received within the third connecting hole;
a pin configured to be received within the second connecting hole; and
a post extending into the hub, the post comprising a groove configured to accept the pin;
wherein movement of the screw causes the hub to rotate about the post.

Clause 34. The blade assembly of clause 33, wherein the hub is adapted to be removably affixed to an arm of a retractor.

Clause 35. The blade assembly of clause 33, wherein the hub comprises a first connecting hole, wherein the first barrel fits within the first connecting hole, the first barrel having a wall and defining a first lumen, a first slot in the wall having a first slope, a first screw having an axis, the first screw fitting within the first lumen of the first barrel, a collar having an inner surface configured to mate with the outer surface of the first screw, the collar having a hole that aligns with the first slot in the wall of the first barrel, and a connecting pin fitting through the hole and the slot such that movement of the collar along the axis causes the first barrel to rotate in a first direction.

Clause 36. A retractor, comprising:
a first arm having a distal end and a proximal end;
a second arm having a distal end and a proximal end;
a first blade coupled near the distal end of the first arm;
a first rotation mechanism that rotates the first blade about a first axis;
a second blade coupled near the distal end of the second arm rotatable about a second axis;
a second rotation mechanism that rotates the second blade about the second axis, wherein the first axis is substantially parallel to the second axis;
a first pivot mechanism in mechanical communication with the first blade and adapted to pivot the first blade about a fourth axis, wherein the first axis is skewed to the fourth axis; and a second pivot mechanism in mechanical communication with the second blade and adapted to pivot the second blade about a fifth axis, wherein the second axis is skewed to the fifth axis.

Clause 37. The retractor of clause 36, further comprising a third blade and a third pivot mechanism in mechanical communication with the third blade and adapted to pivot the third blade about a seventh axis, wherein the seventh axis is skewed to the fourth axis.

Clause 38. A retractor, comprising:
 a first arm having a distal end and a proximal end;
 a second arm having a distal end and a proximal end, at least the distal end of the first arm and the distal end of the second arm being movable toward and away from each other;
 a first blade attached near the distal end of the first arm and a device for moving the first blade about a first axis to adopt at least an opened position and a closed position;
 a second blade attached near the distal end of the second arm and a device for moving the second blade relative a second axis different from the first axis to adopt at least an opened position and a closed position; and
 a device for moving at least the distal end of the first arm and the distal end of the second arm relative to one another along a third axis that is not parallel to the first and second axes.

Clause 39. A retractor blade assembly, comprising:
 a first arm having a distal end and a proximal end;
 a second arm having a distal end and a proximal end, at least the distal end of the first arm and the distal end of the second arm being movable toward and away from each other;
 a first blade attached near the distal end of the first arm and a device for pivoting the first blade about a fourth axis;
 a second blade attached near the distal end of the second arm and a device for pivoting the second blade relative a fifth axis different from the fourth axis; and
 a device for moving at least the distal end of the first arm and the distal end of the second arm relative to one another along a third axis that is not parallel to the fourth and fifth axes.

Clause 40. A method of using a retractor, comprising:
 rotating a first blade of a retractor about a first axis;
 rotating a second blade of a retractor about a second axis, wherein the first axis is substantially parallel to the second axis;
 translating the first blade and the second blade about a third axis pivoting the first blade about a fourth axis, wherein the fourth axis is skewed to the first axis; and
 pivoting the second blade about a fifth axis, wherein the fourth axis is skewed to the second axis.

Clause 41. A method of using a retractor, comprising:
 making an incision in a tissue of a body;
 providing a retractor;
 rotating a first blade of a retractor about a first axis;
 rotating a second blade about a second axis, wherein the first axis is substantially parallel to the second axis;
 pivoting the first blade about a fourth axis, wherein the fourth axis is skewed to the first axis; and
 pivoting the second blade about a fifth axis, wherein the fifth axis is skewed to the second axis.

Clause 42. The method of Clause 41, further comprising positioning the first and second blades substantially parallel to each other to form a first closed blade assembly.

Clause 43. The method of Clause 41, further comprising positioning a third blade substantially parallel to the first and second blades in a closed position.

Clause 44. The method of Clause 43, further comprising pivoting the third blade about a seventh axis, wherein the seventh axis is skewed to the fourth axis.

Clause 45. The method of Clause 43, further comprising inserting the first blade, the second blade, and a third blade within the incision.

Clause 46. The method of Clause 41, further comprising actuating the retractor such that the first blade and second blade are moved apart from one another along a third axis and the incision is stretched along the length of the incision to create an opening longer than the incision.

Clause 47. The method of Clause 41, further comprising actuating the retractor such that the first blade and second blade are slid together along a sixth axis and the incision is stretched along the width of the incision to create an opening wider than the incision.

Clause 48. The method of Clause 41, further comprising creating an aperture in the tissue that is longer and wider than the incision.

Clause 49. A retractor comprising:
 a first blade,
 a first rotation mechanism that rotates the first blade about a first axis,
 a second blade,
 a second rotation mechanism that rotates the second blade about a second axis,
 a first pivot mechanism that pivots the first blade about a fourth axis, wherein the fourth axis is skewed to the first axis;
 a second pivot mechanism that pivots the second blade about a fifth axis, wherein the fifth axis is skewed to the second axis.

Clause 50. The retractor of clause 49, further comprising an actuator that translates the first blade and second blade about a third axis.

Clause 51. The retractor of clause 50, wherein the third axis is perpendicular to the first axis, the second axis or both the first and second axes.

Clause 52. The retractor of clause 49, further comprising an actuator that slides the first blade and second blade about a sixth axis.

Clause 53. The retractor of clause 52, wherein the sixth axis is perpendicular to the first axis, the second axis or both the first and second axes.

Clause 54. The retractor of clause 49, further comprising a third blade.

Clause 55. The retractor of clause 54, wherein at least one of the first, second and third blades is a flat blade.

Clause 56. The retractor of clause 54, wherein at least one blade is removable.

Clause 57. The retractor of clause 54, further comprising a third pivot mechanism that pivots the third blade about a seventh axis, wherein the seventh axis is skewed to the fourth axis.

Clause 58. A method of using a retractor, comprising:
  making an incision in a tissue of a body;
  providing a retractor;
  rotating a first blade of a retractor about a first axis;
  rotating a second blade about a second axis, wherein the first axis is substantially parallel to the second axis;
  pivoting the first blade about a fourth axis, wherein the fourth axis is skewed to the first axis; and
  pivoting the second blade about a fifth axis, wherein the fifth axis is skewed to the second axis.

Clause 59. The method of clause 58, further comprising positioning the first and second blades substantially parallel to each other to form a first closed blade assembly.

Clause 60. The method of clause 58, further comprising positioning a third blade substantially parallel to the first and second blades in a closed position.

Clause 61. The method of clause 60, further comprising pivoting the third blade about a seventh axis, wherein the seventh axis is skewed to the fourth axis.

Clause 62. The method of clause 60, further comprising inserting the first blade, the second blade, and a third blade within the incision.

Clause 63. The method of clause 58, further comprising actuating the retractor such that the first blade and second blade are moved apart from one another along a third axis and the incision is stretched along the length of the incision to create an opening longer than the incision.

Clause 64. The method of clause 58, further comprising actuating the retractor such that the first blade and second blade are slid together along a sixth axis and the incision is stretched along the width of the incision to create an opening wider than the incision.

Clause 65. The method of clause 58, further comprising creating an aperture in the tissue that is longer and wider than the incision.

What is claimed is:

1. A method of using a retractor, comprising:
  making an incision in a tissue of a body;
  inserting a first probe and a second probe into the incision;
  inserting a third blade of a retractor over the first probe and the second probe;
  removing the second probe;
  inserting a shim along the third blade of the retractor, wherein inserting the shim along the third blade of the retractor comprises inserting the shim within a channel of the first probe; and
  removing the first probe.

2. The method of claim 1, further comprising monitoring nerve activity with a first electrode of the first probe.

3. The method of claim 2, further comprising monitoring nerve activity with a second electrode of the second probe.

4. The method of claim 3, wherein the first probe and the second probe comprise a tongue and groove configuration.

5. The method of claim 1, further comprising engaging the shim with notches of the third blade to position the shim in discrete locations.

6. The method of claim 1, further comprising coupling a first blade, a second blade, and the third blade to a body of the retractor.

7. The method of claim 6, further comprising attaching the body of the retractor to a single attachment point.

8. The method of claim 7, further comprising moving the first blade and the second blade relative to the single attachment point.

9. The method of claim 7, further comprising moving the third blade relative to the single attachment point.

10. The method of claim 7, further comprising independently moving the first blade, the second blade, and the third blade relative to the single attachment point.

11. The method of claim 6, further comprising rotating the first blade of the retractor about a first axis and rotating the second blade of the retractor about a second axis.

12. The method of claim 11, further comprising moving the first blade and the second blade apart along a third axis.

13. The method of claim 12, further comprising pivoting the first blade about a fourth axis and pivoting the second blade about a fifth axis.

14. The method of claim 13, further comprising moving the third blade about a sixth axis.

15. The method of claim 1, wherein inserting the shim along the third blade of the retractor comprises inserting the shim within a slot of the third blade.

16. A method of using a retractor, comprising:
  making an incision in a tissue of a body;
  inserting a probe system comprising a first probe and a second probe into the incision;
  inserting a third blade of a retractor along the probe system comprising the first probe and the second probe;
  removing the second probe, wherein the first probe and the third blade of the retractor remain; and
  inserting a shim along the third blade of the retractor, wherein inserting the shim along the third blade of the retractor comprises inserting the shim within a channel of the first probe.

17. The method of claim 16, further comprising removing the first probe, wherein the shim and the third blade of the retractor remain.

18. The method of claim 16, wherein the first probe comprises an electrode.

19. The method of claim 16, wherein the first probe and the second probe comprise a tongue and groove configuration.

20. The method of claim 16, wherein the third blade of the retractor comprises one or more notches configured to maintain the position of the shim relative to the third blade.

* * * * *